United States Patent
Ferrer Montiel et al.

(10) Patent No.: US 10,905,679 B2
(45) Date of Patent: Feb. 2, 2021

(54) TRPM8 RECEPTOR AGONIST COMPOUNDS AND USES THEREOF

(71) Applicant: UNIVERSIDAD MIGUEL HERNANDEZ DE ELCHE, Alicante (ES)

(72) Inventors: Antonio Vicente Ferrer Montiel, Alicante (ES); Asia Fernandez Carvajal, Alicante (ES); Carlos Belmonte Martinez, Alicante (ES); Juana Gallar Martinez, Alicante (ES); Roberto De La Torre, Alicante (ES); Armando Genazzani, Novara (IT); Gian Cesare Tron, Novara (IT); Valentina Mercalli, Novara (IT)

(73) Assignee: UNIVERSIDAD MIGUEL HERNANDEZ DE ELCHE, Alicante (ES)

( * ) Notice: Subject to any disclaimer, the term of this patent is extended or adjusted under 35 U.S.C. 154(b) by 0 days.

(21) Appl. No.: 16/070,820

(22) PCT Filed: Jan. 17, 2017

(86) PCT No.: PCT/ES2017/070026
§ 371 (c)(1),
(2) Date: Jul. 18, 2018

(87) PCT Pub. No.: WO2017/125634
PCT Pub. Date: Jul. 27, 2017

(65) Prior Publication Data
US 2019/0022068 A1 Jan. 24, 2019

(30) Foreign Application Priority Data
Jan. 19, 2016 (ES) .................................. 201630052

(51) Int. Cl.
| | |
|---|---|
| *C07D 249/04* | (2006.01) |
| *C07D 249/06* | (2006.01) |
| *C07D 401/04* | (2006.01) |
| *H02G 3/08* | (2006.01) |
| *H02G 3/06* | (2006.01) |
| *A61K 31/4192* | (2006.01) |
| *A61P 27/04* | (2006.01) |
| *A61P 15/02* | (2006.01) |

(52) U.S. Cl.
CPC .......... *A61K 31/4192* (2013.01); *A61P 15/02* (2018.01); *A61P 27/04* (2018.01); *C07D 249/04* (2013.01); *C07D 249/06* (2013.01); *C07D 401/04* (2013.01); *H02G 3/0675* (2013.01); *H02G 3/088* (2013.01)

(58) Field of Classification Search
CPC ...................... C07D 249/04–06; C07D 401/04
See application file for complete search history.

(56) References Cited

U.S. PATENT DOCUMENTS

2015/0376136 A1 12/2015 Chumakova et al.

FOREIGN PATENT DOCUMENTS

| EP | 2614860 A2 | 7/2013 |
| EP | 3406600 A1 | 11/2018 |

OTHER PUBLICATIONS

Khaligh et al., Chem. Pharm. Bull., 64, 1589-1596 (2016).*
No Author. "TRPM8_HUMAN" (Sequence Listing) [online] retrieved Jul. 22, 2015 from https://www.uniprot.org/uniprot/Q7Z2W7. 1 page.
Altschul et al. "Basic local alignment search tool." Journal of Molecular Biology 215.3 (1990): 403-410.
Bödding et al. "Characterisation of TRPM8 as a pharmacophore receptor." Cell Calcium 42.6 (2007): 618-628.
Fernández-Peña et al. "Targeting TRPM8 for pain relief." The Open Pain Journal. 2013, 6 (Suppl 1: M15) pp. 154-164.
Mohan et al. "Synthesis and structures of (−) menthyl and (+) neomenthyl substituted enantio pure bis (1, 2, 3-triazol-5-ylidene) Pdl 2 complexes and PEPPSI type (1, 2, 3-triazol-5-ylidene)(pyridine) Pdl 2 complexes. Comparison of catalytic activities for C—C coupling." Journal of Organometallic Chemistry 799 (2015): 115-121.
Nagender et al. "Studies on Synthesis of Novel Triazolalkyl Tagged Trifluoromethyl Substituted Pyrimidine Derivatives and their Evaluation for Cytotoxic Activity." Letters in Drug Design & Discovery 10.9 (2013): 865-871.
Parra, Andres, et al. "Tear fluid hyperosmolality increases nerve impulse activity of cold thermoreceptor endings of the cornea." PAIN® 155.8 (2014): 1481-1491.

(Continued)

*Primary Examiner* — Alicia L Otton
(74) *Attorney, Agent, or Firm* — K&L Gates LLP; Louis C. Cullman; Benjamin D. Heuberger

(57) ABSTRACT

The invention relates to compounds having formula (I) wherein A is selected from the group consisting of: a) optionally substituted ($C_1$-$C_8$) alkyl; b) optionally substituted ($C_3$-$C_6$) cycloalkyl; c) optionally substituted ($C_6$-$C_{14}$) aryl; d) optionally substituted ($C_6$-$C_{14}$) heteroaryl; e) C(O)—($C_6$-$C_{14}$) aryl, in which group ($C_6$-$C_{14}$) aryl is optionally substituted; f) C(O)—($C_6$-$C_{14}$) heteroaryl, in which group ($C_6$-$C_{14}$) heteroaryl is optionally substituted; g) CH(OH)—($C_6$-$C_{14}$) aryl, in which group ($C_6$-$C_{14}$) aryl is optionally substituted; and h) CH(OH)—($C_6$-$C_{14}$) heteroaryl, in which group ($C_6$-$C_{14}$) heteroaryl is optionally substituted. The invention also relates to methods for the production of said compounds, to pharmaceutical and veterinary compositions comprising said compounds and to the therapeutic uses thereof, such as for the prevention and/or treatment of dry eye syndrome, vaginal dryness and/or burning mouth syndrome.

20 Claims, 1 Drawing Sheet

(56) References Cited

OTHER PUBLICATIONS

Utsintong et al. "Parallel synthesis of "Click" chalcones as antitubulin agents." Medicinal Chemistry 9.4 (2013): 510-516.
Welschoff et al. "Practical Synthesis of Optically Pure Menthylamines Starting from Racemic Neomenthol." Synthesis 2010.21 (2010): 3596-3601.
Foye. "Chapter 9: Physicochemical and Biopharmaceutical Properties." Foye's Principles of Medicinal Chemistry. Lippincott Williams & Wilkins, 2008. 2 pages.
International Search Report in corresponding International Patent Application No. PCT/ES2017/070026, dated Apr. 24, 2017. 2 pages.
Extended European Search Report in corresponding European Patent Application No. 17741136.0 dated Apr. 12, 2019. 6 pages.

* cited by examiner

TRPM8 RECEPTOR AGONIST COMPOUNDS AND USES THEREOF

CROSS-REFERENCE TO RELATED PATENT APPLICATIONS

This application is a U.S. National Stage Application under 35 U.S.C. § 371 of International Patent Application No. PCT/ES2017/070026, filed Jan. 17, 2017, the entire content of which is incorporated herein by reference, which claims the benefit of priority under 35 U.S.C. Section 119(e) of Spanish Patent Application number P201630052 filed Jan. 19, 2016. The International Application was published on Jul. 27, 2017, as International Publication No. WO 2017/125634 AI.

The invention relates to TRPM8 receptor agonist compounds, to methods for preparing same and to pharmaceutical and veterinary compositions that comprise said compounds. It also relates to the uses of these compounds, in particular, the therapeutic uses thereof, such as for example, the prevention and/or treatment of dry eye syndrome, vaginal dryness and/or burning mouth syndrome.

PRIOR ART

The TRPM8 receptor or "Transient receptor potential cation channel subfamily M member 8", also known as the cold and menthol receptor 1 (or "CMR14"), is a protein that in humans is encoded by the TRPM8 gene. The TRPM8 receptor is an ion channel which, once activated, allows the entry of sodium ($Na^+$) and calcium ($Ca^{2+}$) to the cell, leading to a depolarisation of the same that results in a change in the potential of the membrane.

The TRPM8 protein is expressed in sensory neurons and is activated by low temperatures (below about 26° C.), by chemical agents, such as menthol and icilin, and by voltage. TRPM8 is also expressed in the prostate, lungs and bladder and is overexpressed in various cancer cell lines.

Dry eye syndrome or xerophthalmia is a painful condition caused by an inadequate tear film or by an alteration in the ocular surface. It is a common ophthalmological problem, particularly in the elderly population, which leads to persistent ocular discomfort and can also diminish visual function. The aetiology and mechanisms involved in dry eye disease are uncertain, but ultimately converge on alterations in the tear film that protects the surface of the cornea. Recent studies have shown that TRPM8 activation plays a fundamental role in the regulation of basal tear secretion in mice (Parra A et al, Pain. 2014, 155(8), 1481-91).

Other related diseases that present with dry mucous surfaces may also benefit from these observations. Examples of these diseases or conditions would include burning mouth syndrome, which is often a condition of idiopathic origin that is characterised by burning, itching, stinging and pain in the mouth that affects 1.5 to 5.5% of middle-aged and elderly women, and vaginal dryness which, although it can occur at any age, affects about 50% of women aged between 40 and 50 (Carlos Fernandez-Pea et al., The Open Pain Journal, 2013, 6, (Suppl 1: M15) 154-164).

Although TRPM8 agonists are known, it would be desirable to develop novel TRPM8 agonists that can be used, among other applications, as active substances in drugs.

EXPLANATION OF THE INVENTION

The inventors have discovered that the substituted triazoles of formula (I) are TRPM8 receptor agonists and activate the TRPM8 channels, both in vitro and in vivo, as is shown in detail in the examples. Therefore, said compounds are particularly useful in the prevention and/or treatment of dry eye syndrome, vaginal dryness and/or burning mouth syndrome.

Thus, one aspect of the invention relates to a compound of formula (I) or to a pharmaceutically acceptable salt thereof, or to any stereoisomer or mixture of stereoisomers, whether of the compound of formula (I) or of any of the pharmaceutically acceptable salts thereof

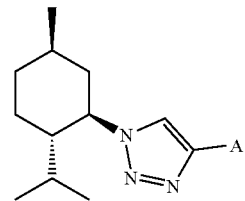

(I)

wherein:

A is selected from the group consisting of:
a) ($C_1$-$C_8$) alkyl optionally substituted by one or more substituents selected between $R^1$ and ($C_6$-$C_{14}$) aryl optionally substituted by one or more substituents $R^2$;
b) ($C_3$-$C_6$) cycloalkyl optionally substituted by one or more substituents $R^1$;
c) ($C_6$-$C_{14}$) aryl optionally substituted by one or more substituents $R^3$;
d) ($C_6$-$C_{14}$) heteroaryl optionally substituted by one or more substituents $R^3$;
e) C(O)—($C_6$-$C_{14}$) aryl, wherein the ($C_6$-$C_{14}$) aryl group is optionally substituted by one or more substituents $R^3$;
f) C(O)—($C_6$-$C_{14}$) heteroaryl, wherein the ($C_6$-$C_{14}$) heteroaryl group is optionally substituted by one or more substituents $R^3$;
g) CH(OH)—($C_6$-$C_{14}$) aryl, wherein the ($C_6$-$C_{14}$) aryl group is optionally substituted by one or more substituents $R^3$; and
h) CH(OH)—($C_6$-$C_{14}$) heteroaryl, wherein the ($C_6$-$C_{14}$) heteroaryl group is optionally substituted by one or more substituents $R^3$;

each $R^1$ is selected independently from the group consisting of a halogen atom, —$OR^4$, —CN, —$COOR^4$, —$CONR^4R^5$, —$NR^4R^5$, —$NHCOR^4$, —$NHSO_2R^4$, —S(O)$R^4$, —$S(O)_2R^4$, and —$SO_2NHR^4$;

each $R^2$ is selected independently from the group consisting of a halogen atom, —COOH, —OH, —$NH_2$, —$COOR^6$, —$NO_2$, —$CF_3$, —$OCF_3$, —CN, —$OR^6$, —$CONH_2$, —$CONHR^6$, —$CONR^6R^7$, —$NHR^6$, —$NHCOR^6$, —$NHSO_2R^6$, and —$SO_2NHR^6$;

each $R^3$ is selected independently from the group consisting of a halogen atom, ($C_6$-$C_{14}$) aryl optionally substituted by one or more substituents $R^2$, —$CF_3$, —$COOR^4$, —$CONR^4R^5$, —CN, —$NHR^4$, —$NHCOR^4$, —$NHSO_2R^4$, —$NO_2$, —$OR^4$, —$OCF_3$, and —$SO_2NHR^4$;

$R^4$ and $R^5$ are selected independently from the group consisting of H, ($C_1$-$C_8$) alkyl optionally substituted by one or more substituents $R^8$, ($C_3$-$C_6$) cycloalkyl optionally substituted by one or more substituents $R^8$, ($C_6$-$C_{14}$) aryl optionally substituted by one or more substituents $R^2$, and ($C_6$-$C_{14}$) heteroaryl optionally substituted by one or more substituents $R^2$;

$R^6$ and $R^7$ are selected independently from the group consisting of H, ($C_1$-$C_8$) alkyl optionally substituted by one or more substituents R⁸ and $(C_3-C_6)$ cycloalkyl optionally substituted by one or more substituents R⁸; and each R⁸ is selected independently from the group consisting of —COOH, —OH, —NH₂, NHR⁹, -halogen, —COOR⁹, —NO₂, —CF₃, —OCF₃, —CN, —OR⁹, —CONH₂; and R⁹ is selected from the group consisting of H, $(C_1-C_8)$ alkyl optionally substituted by one or more halogen atoms and $(C_3-C_6)$ cycloalkyl optionally substituted by one or more halogen atoms;

with the condition that the compound of formula (I) is different from 4-[[1-[5-methyl-2-(1-methyl-ethyl)cyclohexyl]-1H-1,2,3-triazole-4-yl]methoxy]-6-(trifluoromethyl)-2-pyrimidinamine.

The 4-[[1-[5-methyl-2-(1-methyl-ethyl)cyclohexyl]-1H-1,2,3-triazole-4-yl]methoxy]-6-(trifluoromethyl)-2-pyrimidinamine compound corresponds to compound 5c of the document Nagender P. et al, Letters in Drug Design & Discovery, 2013, 10,000-000. This document is not related to TRPM8 or to dry eye syndrome, vaginal dryness and/or burning mouth syndrome.

The terms used throughout the description should be understood according to their conventional meaning as known in the prior art, unless otherwise specified.

The term "halogen" or "halo" refers to an atom selected among F, Cl, Br and I.

The term "$(C_1-C_8)$ alkyl" refers to a fully saturated straight or branched hydrocarbon chain radical, which consists of carbon and hydrogen atoms, which has 1 to 8 carbon atoms. Illustrative, non-limiting examples of $(C_1-C_8)$ alkyl include methyl, ethyl, n-propyl, i-propyl, n-butyl, t-butyl, n-pentyl, n-hexyl, etc.

The term "$(C_3-C_6)$ cycloalkyl" refers to a carbocyclic radical obtained by removing one hydrogen from a cycloalkane, which has 3 to 6 carbon atoms. Illustrative, non-limiting examples of $(C_3-C_6)$ cycloalkyl include cyclopropyl, cyclobutyl, cyclopentyl or cyclohexyl.

The term "$(C_6-C_{14})$ aryl" refers to an aromatic carbocyclic chain radical, which consists only of carbon and hydrogen atoms, which has 6 to 14 carbon atoms, which can have a single ring or multiple rings (up to three rings) which, in the latter case, are condensed and/or covalently bonded. Illustrative, non-limiting examples of aryl include phenyl, naphthyl, anthracenyl, phenanthrenyl, etc.

The term "$(C_6-C_{14})$ heteroaryl" refers to an aromatic ring structure in which at least one of the atoms of the aromatic ring is a heteroatom selected from the group formed by nitrogen, oxygen and sulphur, wherein the nitrogen and sulphur atom or atoms are optionally oxidised, and the nitrogen atom or atoms are optionally quaternised; heteroaryl groups can be joined to the rest of the molecule via a heteroatom whenever chemically possible. A heteroaryl may be made up of a single ring or of two or more fused rings. Illustrative, non-limiting examples of heteroaryl include pyrrolyl, pyrazolyl, imidazolyl, pyrazinyl, oxazolyl, isoxazolyl, thiazolyl, furyl, thienyl, pyridyl, pyrimidyl, indolyl, isoindolyl, quinolyl, isoquinolyl, etc.

The term "substituted by one or more" means that a group may be substituted by one or more, preferably by 1, 2, 3 or 4, substituents, provided that this group has sufficient positions capable of being substituted.

The compounds of formula (I) may be in salt form. The term "salt", as used herein, comprises any stable salt that the compounds of formula (I) are capable of forming. Pharmaceutically acceptable salts, i.e. non-toxic salt forms that can be administered to a subject and directly or indirectly provide a compound of formula (I), are preferred.

The salts of the compounds of formula (I) can be prepared by methods known in the prior art from a compound of formula (I) which contains a basic or acidic moiety using conventional chemical methods. Such salts are generally prepared by reacting the base or free acid forms of those compounds with a stoichiometric amount of the appropriate base or acid in water or in an organic solvent (e.g. ether, ethyl acetate, ethanol, isopropanol, etc.) or in a mixture of both. By way of illustration, acid addition salts can be obtained by treating the base form with appropriate acids such as inorganic acids, for example, hydracids such as hydrochloric acid, hydrobromic acid and the like; sulphuric acid; nitric acid; phosphoric acid and the like; or organic acids, e.g. acetic, propanoic, hydroxyacetic, 2-hydroxypropanoic, 2-oxopropanoic, oxalic, malonic, succinic, maleic, fumaric, malic, tartaric, 2-hydroxy-1,2,3-propane-tricarboxylic, methanesulphonic, ethanesulphonic, benzenesulphonic, 4-methyl-benzenesulphonic, p-toluenesulphonic, cyclohexanesulphamic, 2-hydroxybenzoic, 4-amino-2-hydroxybenzoic acid and similar acids. Likewise, the salts can be converted by treatment with a base in the form of a free base.

The compounds of formula (I) that contain an acidic proton can also be converted into non-toxic metal salts or amine addition salts by treatment with appropriate organic and inorganic bases. Suitable base salts comprise, for example, ammonium salts, alkali metal and alkaline-earth metal salts, for example lithium, sodium, potassium, magnesium, calcium salts and the like, salts with organic bases, for example ethylenediamine, ethanolamine, N,N-dialkylethanolamine, triethanolamine, glucamine, benzathine, N-methyl-D-glucamine, hydrabamine salts, etc., and salts with amino acids such as, for example, arginine, lysine and the like.

The compounds represented by formula (I) described above, can include stereoisomers depending on the presence of chiral centres. The individual isomers, enantiomers or diastereomers and mixtures thereof in any proportion fall within the scope of the present invention. Unless otherwise mentioned or indicated, the chemical designation of a compound comprises the mixture of all possible isomeric forms that said compound may possess. Said mixture may contain all the diastereomers and/or enantiomers of the basic molecular structure of said compound. All stereochemically isomeric forms of the compounds of formula (I) of the present invention, both in pure form and mixed together, are within the scope of the present invention.

The pure stereoisomeric forms of the compounds as mentioned in the present invention are defined as isomers substantially free of other enantiomeric or diastereomeric forms of the same basic molecular structure of said compounds. In particular, the term "pure stereoisomeric form" or "stereochemically pure isomeric form" refers to compounds having a stereoisomeric excess of at least 80% (i.e. a minimum of 80% of one isomer and a maximum of 20% of the other possible isomers) up to a stereoisomeric excess of 100% (i.e. 100% of one isomer and none of the other), more particularly, compounds or intermediate products having a stereoisomeric excess from 90% up to 100%, even more particularly having a stereoisomeric excess from 95% up to 100% and even more particularly having a stereoisomeric excess from 98% up to 100%. The terms "enantiomerically pure" and "diastereomerically pure" should be understood in a similar manner, but considering the enantiomeric excess and the diastereomeric excess, respectively, of the mixture in question.

The pure stereoisomeric forms of the compounds of formula (I) can be obtained by applying methods that are known in the prior art. By way of illustration, the enantiomers can be separated from one another by selective or fractional crystallisation of the diastereomeric salts thereof with optically active acids or bases (e.g. tartaric acid, dibenzoyltartaric acid, ditoluoyltartaric acid, camphorsulphonic acid, etc.) and subsequent release of the enantiomers by treatment with alkali or acid. Alternatively, the enantiomers can be separated by chromatographic techniques, advantageously by liquid chromatography using a chiral stationary phase. Likewise, said pure stereoisomeric forms can also derive from the corresponding pure stereoisomeric forms of the appropriate starting materials, as long as the reaction takes place stereospecifically. If a specific stereoisomer is to be achieved, said compound will be synthesised by stereospecific preparation methods. These methods will advantageously use enantiomerically pure starting materials.

The diastereomeric racemates of the compounds of formula (I) can be obtained separately by conventional methods. The appropriate physical separation methods that can be used advantageously include, among others, selective crystallisation and chromatography, for example, column chromatography.

The compounds of formula (I) may be in crystalline form, either as free compounds or as solvates, and both forms are intended to be within the scope of the present invention. The term "solvate", as used herein, refers to the crystal forms of the compounds of formula (I) that contain stoichiometric or non-stoichiometric amounts of solvent. Since water is a solvent, the solvates also include hydrates. Illustrative, non-limiting examples of solvates include hydrates and alcoholates such as methanolates or ethanolates. In a particular embodiment, the solvate is a pharmaceutically acceptable solvate. The solvation methods are known to a person skilled in the art.

Compounds of formula (I), comprising one or more isotopically enriched atoms, are also part of the invention, including for example compounds of formula (I) in which a hydrogen atom has been replaced with a deuterium or tritium atom, or a carbon or nitrogen atom has been replaced with carbon enriched in $^{13}C$ or $^{14}C$ or nitrogen enriched in 15N, respectively. In addition, the compounds of formula (I) are also part of the invention, containing non-natural proportions of atomic isotopes in one or more of the atoms constituting such compounds. For example, the compounds may be radiolabelled with radioactive isotopes, for example such as $^{3}H$, $^{14}C$, $^{15}N$, $^{35}S$, $^{90}Y$, $^{99}Tc$, $^{111}I$, $^{125}I$, $^{131}I$. It is intended for all isotopic variations of the compounds of the present invention, radioactive or not, to fall within the scope of the present invention.

The present invention also includes prodrugs of the compounds of formula (I). The term "prodrug", as used herein, refers to the pharmacologically acceptable derivatives of the compounds of formula (I), such as, for example, esters, amides and phosphates, so that the product of the derivative resulting from in vivo biotransformation is the active drug as defined in the compounds of formula (I). The reference of Foye's principles of Medicinal Chemistry, Lippicott Williams & Wilkins, Ed. 2008, page 223, which generally describes prodrugs, is incorporated into the present description by reference. Prodrugs preferably have excellent aqueous solubility, higher bioavailability and are easily metabolised in active inhibitors in vivo. A prodrug of a compound of formula (I) can be easily prepared by appropriately modifying functional groups present in the compound of formula (I).

In a particular embodiment, optionally in combination with one or more features of any of the embodiments described in this invention, in the compound of formula (I), A is selected from the group consisting of:
a) $(C_1-C_8)$ alkyl optionally substituted by one or more substituents selected between $R^1$ and $(C_6-C_{14})$ aryl optionally substituted by one or more substituents $R^2$;
b) $(C_3-C_6)$ cycloalkyl optionally substituted by one or more substituents $R^1$;
c) $(C_6-C_{14})$ aryl optionally substituted by one or more substituents $R^3$;
d) $(C_6-C_{14})$ heteroaryl optionally substituted by one or more substituents $R^3$;
e) $C(O)$—$(C_6-C_{14})$ aryl, wherein the $(C_6-C_{14})$ aryl group is optionally substituted by one or more substituents $R^3$; and
g) $CH(OH)$—$(C_6-C_{14})$ aryl, wherein the $(C_6-C_{14})$ aryl group is optionally substituted by one or more substituents $R^3$;
wherein, in the previous groups, $R^1$, $R^2$ and $R^3$ have the previously described meanings.

In another particular embodiment, optionally in combination with one or more features of any of the embodiments described in this invention, in the compound of formula (I), A is selected from the group consisting of:
a) $(C_1-C_8)$ alkyl optionally substituted by one or more substituents selected between $R^1$ and $(C_6-C_{14})$ aryl optionally substituted by one or more substituents $R^2$;
c) $(C_6-C_{14})$ aryl optionally substituted by one or more substituents $R^3$;
d) $(C_6-C_{14})$ heteroaryl optionally substituted by one or more substituents $R^3$; and
e) $C(O)$—$(C_6-C_{14})$ aryl, wherein the $(C_6-C_{14})$ aryl group is optionally substituted by one or more substituents $R^3$;
wherein, in the previous groups, $R^1$, $R^2$ and $R^3$ have the previously described meanings.

In another particular embodiment, optionally in combination with one or more features of any of the embodiments described in this invention, in the compound of formula (I), A is: a) $(C_1-C_8)$ alkyl optionally substituted by one or more substituents selected between $R^1$ and $(C_6-C_{14})$ aryl optionally substituted by one or more substituents $R^2$; wherein, in the previous groups, $R^1$ and $R^2$ have the previously described meanings. In a more particular embodiment, A is $(C_1-C_8)$ alkyl optionally substituted by one or more substituents selected from the group consisting of $OR^4$, —CN, —COOR$^4$, and $(C_6-C_{14})$ aryl, more particularly phenyl, optionally substituted by one or more substituents $R^2$; wherein $R^4$ and $R^2$ have the previously described meanings. In an even more particular embodiment, A is $(C_1-C_8)$ alkyl optionally substituted by one or more substituents selected from the group consisting of $OR^4$, —CN, —COOR$^4$, and phenyl optionally substituted by one or more substituents $R^2$; wherein each $R^4$ is, independently, H or methyl, and wherein $R^2$ has the previously described meanings. In an even more particular embodiment, A is $(C_1-C_8)$ alkyl optionally substituted by phenyl optionally substituted by one or more substituents $R^2$; wherein $R^2$ has the previously described meanings. In another particular embodiment, in the compound of formula (I), A is —CH$_2$OH, —CH$_2$—O—CH$_3$, —(CH$_2$)S—COOH, —(CH$_2$)$_4$—CN or phenethyl (—CH$_2$—CH$_2$-phenyl).

In another particular embodiment, optionally in combination with one or more features of any of the embodiments described in this invention, in the compound of formula (I), A is b) $(C_3-C_6)$ cycloalkyl optionally substituted by one or more substituents $R^1$; wherein $R^1$ has the previously described meanings. In a more particular embodiment, $(C_3-$ $C_6$) cycloalkyl is cyclopropane, cyclobutane or cyclohexane. In another even more particular embodiment, A is ($C_3$-$C_6$) cycloalkyl substituted by —$OR^4$, wherein $R^4$ is H. In an even more particular embodiment, in the compound of formula (I), A is 1-hydroxycyclohexyl.

In another particular embodiment, optionally in combination with one or more features of any of the embodiments described in this invention, in the compound of formula (I), A is c) ($C_6$-$C_{14}$) aryl optionally substituted by one or more substituents $R^3$; wherein $R^3$ has the previously described meanings. In a more particular embodiment, A is unsubstituted ($C_6$-$C_{14}$) aryl, in particular phenyl or naphthyl, more particularly phenyl. In another particular embodiment, A is ($C_6$-$C_{14}$) aryl substituted by one or more substituents $R^3$; wherein $R^3$ has the previously described meanings. In a more particular embodiment, A is ($C_6$-$C_{14}$) aryl, in particular phenyl or naphthyl, substituted by one or more substituents selected between —$OR^4$ and ($C_6$-$C_{14}$) aryl optionally substituted by one or more substituents $R^2$, wherein $R^2$ and $R^4$ have the previously described meanings. In an even more particular embodiment, A is ($C_6$-$C_{14}$) aryl, in particular phenyl, substituted by one or more substituents selected between —$OR^4$ and unsubstituted ($C_6$-$C_{14}$) aryl, more particularly unsubstituted phenyl $R^4$, wherein a choice is made between H, ($C_1$-$C_8$) alkyl and ($C_6$-$C_{14}$) aryl. In an even more particular embodiment, A is ($C_6$-$C_{14}$) aryl, in particular phenyl, substituted by one or more substituents —$OR^4$, wherein $R^4$ is ($C_1$-$C_8$) alkyl. In an even more particular embodiment, A is phenyl, phenylphenyl (e.g. biphenyl), naphthyl, hydroxyphenyl (e.g. 3-hydroxyphenyl, etc.), methoxyphenyl (e.g. 3-methoxyphenyl, 4-methoxyphenyl, etc.), dimethoxyphenyl (e.g. 3,5-dimethoxyphenyl, etc.), or phenoxyphenyl.

In another particular embodiment, optionally in combination with one or more features of any of the embodiments described in this invention, in the compound of formula (I), A is d) ($C_6$-$C_{14}$) heteroaryl, more particularly ($C_6$) heteroaryl, optionally substituted by one or more substituents $R^3$; wherein $R^3$ has the previously described meanings. In another particular embodiment, in the compound of formula (I), A is unsubstituted ($C_6$-$C_{14}$) heteroaryl, more particularly unsubstituted ($C_6$) heteroaryl. In a more particular embodiment, in the compound of formula (I), A is pyridyl.

In another particular embodiment, optionally in combination with one or more features of any of the embodiments described in this invention, in the compound of formula (I), A is e) C(O)—($C_6$-$C_{14}$) aryl, wherein the ($C_6$-$C_{14}$) aryl group is, in particular, phenyl and is optionally substituted by one or more substituents $R^3$; wherein $R^3$ has the previously described meanings. In an even more particular embodiment, in the compound of formula (I), A is:

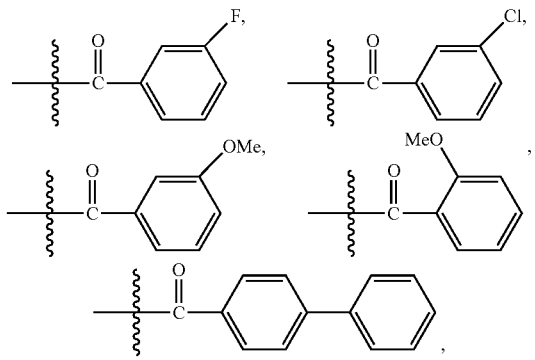

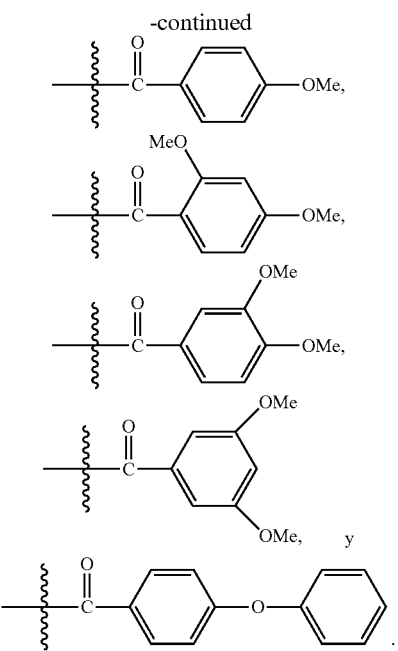

In another particular embodiment, optionally in combination with one or more features of any of the embodiments described in this invention, in the compound of formula (I), A is g) CH(OH)—($C_6$-$C_{14}$) aryl, wherein the ($C_6$-$C_{14}$) aryl group is, in particular, phenyl and is optionally substituted by one or more substituents $R^3$; wherein $R^3$ has the previously described meanings. In a more particular embodiment, A is CH(OH)—($C_6$-$C_{14}$) aryl, wherein ($C_6$-$C_{14}$) aryl is, in particular, phenyl and is substituted by one or more substituents —$OR^4$, wherein $R^4$ has the previously described meanings, more particularly $R^4$ is ($C_1$-$C_8$) alkyl. In an even more particular embodiment, in the compound of formula (I), A is:

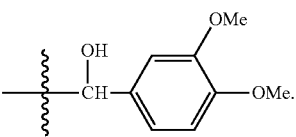 [SMILES: *C(O)c1ccc(OC)c(OC)c1]

In another particular embodiment, the compound of formula (I) is selected from the group consisting of: (1-((1R,2S,5R)-2-isopropyl-5-methylcyclohexyl)-1H-1,2,3-triazole-4-yl)methanol (Compound TZM-1); 1-((1R,2S,5R)-2-isopropyl-5-methylcyclohexyl)-4-(4-phenoxyphenyl)-1H-1,2,3-triazole (Compound TZM-2); 1-((1R,2S,5R)-2-isopropyl-5-methylcyclohexyl)-4-phenyl-1H-1,2,3-triazole (Compound TZM-3); 1-((1R,2S,5R)-2-isopropyl-5-methylcyclohexyl)-4-(4-methoxyphenyl)-1H-1,2,3-triazole (Compound TZM-4); 4-([1,1'-biphenyl]-4-yl)-1-((1R,2S,5R)-2-isopropyl-5-methylcyclohexyl)-1H-1,2,3-triazole (Compound TZM-5); 1-(1-((1R,2S,5R)-2-isopropyl-5-methylcyclohexyl)-1H-1,2,3-triazole-4-yl)cyclohexan-1-ol (Compound TZM-6); 4(3,5-dimethoxyphenyl)-1-((1R,2S,5R)-2-isopropyl-5-methylcyclohexyl)-1H-1,2,3-triazole (Compound TZM-7); 1-((1R,2S,5R)-2-isopropyl-5-methylcyclohexyl)-4-(naphthalene-1-yl)-1H-1,2,3-triazole (Compound TZM-8); 2-(1-((1R,2S,5R)-2-isopropyl-5-methylcyclohexyl)-1H-1,2,3-triazole-4-yl)pyridine (Compound TZM-9); 1-((1R,2S,5R)-2-isopropyl-5-methylcyclohexyl)-4-phenethyl-1H-1,2,3-triazole (Compound TZM-10); (3,4-dimethoxyphenyl) (1-((1R,2S,5R)-2-isopropyl-5-methylcyclohexyl)-1H-1,2,3-triazole-4-yl)methanone (Compound TZM-11); (3-fluorophenyl) (1-((1R,2S,5R)-2-isopropyl-5-methylcyclohexyl)-1H-1,2,3-triazole-4-yl)methanone (Compound TZM-12); (1-((1R,2S,5R)-2-isopropyl-5-methylcyclohexyl)-1H-1,2,3-triazole-4-yl) (4-phenoxyphenyl)methanone (Compound TZM-13); (1-((1R,2S,5R)-2-isopropyl-5-methylcyclohexyl)-1H-1,2,3-triazole-4-yl)(2-methoxyphenyl)methanone (Compound TZM-15); (4-chlorophenyl)(1-((1R,2S,5R)-2-isopropyl-5-methylcyclohexyl)-1H-1,2,3-triazole-4-yl)methanone (Compound TZM-20); 9-(1-((1R,2S,5S)-2-isopropyl-5-methylcyclohexyl)-1H-1,2,3-triazole-4-yl)nonanoic acid (Compound TZM-21); 5-(1-(((1R,2S,5S)2-isopropyl-5-methylcyclohexyl)-1H-1,2,3-triazole-4-yl)pentanenitrile (Compound TZM-22); 3-[1-((1R,2S,5R)-2-isopropyl-5-methylcyclohexyl)-1H-1,2,3-triazole-4-yl]phenol (Compound TZM-23); 1-((1R,2S,5R)-2-isopropyl-5-methylcyclohexyl)-4-(methoxymethyl)-1H-1,2,3-triazole (Compound TZM-25); and (3,4-dimethoxyphenyl) (1-((1R,2S,5R)-2-isopropyl-5-methylcyclohexyl)-1H-1,2,3-triazole-4-yl)methanol (Compound TZM-26).

Another aspect of the invention relates to a method for preparing the compound of formula (I) as defined above, which comprises the following steps:

a) reacting the compound (1S,2R,4R)-2-azido-1-isopropyl-4-methylcyclohexane [compound of formula (II):

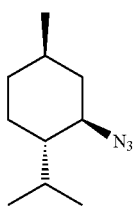

(II)

with an alkyne of formula (III):

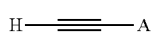

(III)

wherein A has the meanings indicated previously in relation to the compound of formula (I); and b) optionally converting the compound of formula (I) obtained in the previous step into another compound of formula (I) in one or more steps; and/or c) optionally reacting a compound of formula (I) obtained with a base or an acid to give the corresponding salt.

The reaction between the compound of formula (II) and the compound of formula (III) can be carried out in the presence of sodium ascorbate and a cupric salt in a suitable solvent that can comprise one or more solvents, for example two solvents. In some embodiments, the solvents are water and an organic solvent. In some embodiments, the organic solvent is an organic solvent miscible with water, for example a $(C_1-C_6)$ alcohol. In some embodiments, the reaction can take place at a temperature between 0° C. and 10° C. for a period of time comprised between 1 h and 24 h.

The reaction between the compound of formula (II) and the compound of formula (III) is advantageously carried out in an aqueous-organic reaction medium comprising water and an organic solvent, such as a lower alcohol, to which sodium ascorbate is added to reduce copper (II) to copper (I) and a cupric salt (II), at a temperature comprised between 0° C. and 50° C. for a period of time comprised between 1 h and 24 h, preferably with agitation; next, the reaction mixture is diluted with water and cooled, and the resulting precipitate is collected by filtration; alternatively, the triazole of formula (I) can be precipitated by evaporating the solvent and purifying by chromatography. In a particular embodiment, one equivalent (eq) of the compound of formula (II) is reacted with 1 eq of the compound of formula (III) in a medium comprising water:tert-butanol in a 1:1 ratio (v:v); sodium ascorbate (0.1 eq) from a 1 M aqueous solution and copper (II) sulphate pentahydrate (0.01 eq), which acts as a source of copper (II) that is reduced in situ to copper (I) by sodium ascorbate, are added to said mixture, and the resulting reaction is agitated at room temperature for 24 hours. After this period of time, the reaction mixture is diluted with water, cooled on ice, and the resulting precipitate is collected by filtration, or, alternatively, when the addition of water does not result in the precipitation of the triazole, the solvent is evaporated and purification is carried out by chromatography or other techniques such as magnetic resonance or mass spectrometry.

The compound of formula (II) is a known compound that can be prepared according to the method published in Welschoff N. et al. Synthesis 2010, 3596-3601. The alkynes of formula (III) were purchased commercially from Sigma-Aldrich or prepared as described in Utsintong M. et al. *Med. Chem.* 2013, 9, 510-516.

Another aspect of the invention relates to a pharmaceutical or veterinary composition comprising a therapeutically effective amount of the compound of formula (I) as defined above, together with one or more pharmaceutically or veterinarily acceptable excipients, adjuvants or vehicles.

The terms pharmaceutically or veterinarily acceptable "excipient", "adjuvant", or "vehicle" refer to molecular entities or substances used to administer an active substance (e.g. a compound of formula (I)), including but not limited to binders, flavourings, fillers, dyes, preservatives, diluents, disintegrants, humectants, buffers, etc., which may be present in the pharmaceutical or veterinary composition of the invention. Such pharmaceutically or veterinarily acceptable excipients, adjuvants or vehicles can be sterile liquids, such as waters and oils, including those of petroleum or animal, vegetable or synthetic origin, such as peanut oil, soybean oil, mineral oil, sesame oil and the like, etc., or solids, such as magnesium and calcium carbonates, carboxymethyl cellulose, starches, sugars, gums, magnesium stearate or calcium, etc. A wide variety of pharmaceutically or veterinarily acceptable excipients, adjuvants or vehicles are available for pharmaceutical dosage forms and the selection of suitable excipients, adjuvants or vehicles is part of the routine practice of a person skilled in the art of pharmaceutical formulation.

In a particular embodiment, the pharmaceutical or veterinary composition of the invention can be a solid (e.g. tablets, capsules, coated tablets, granules, suppositories, sterile crystalline or amorphous solids that can be reconstituted to provide liquid forms, etc.), liquid (e.g. solutions, suspensions, emulsions, elixirs, lotions, ointments, etc.), or semi-solid (e.g. gels, ointments, creams and the like) form.

The pharmaceutical or veterinary composition of the invention can be administered by different routes, for example, oral, parenteral (e.g. intradermal, intramuscular, intraperitoneal, intravenous, subcutaneous, etc.), topical, ophthalmic, buccal, vaginal, etc., and can be administered locally or systemically or directly to the target site.

In a particular embodiment, the pharmaceutical or veterinary composition of the invention is administered by the ophthalmic route (e.g. eye drops, ointment, ophthalmic drops, etc.), in particular when it is used in the treatment and/or prevention of xerophthalmia or dry eye syndrome.

In another particular embodiment, the pharmaceutical or veterinary composition of the invention is administered vaginally (e.g. bolus, cream, gel, ointment, etc.), in particular when used in the treatment and/or prevention of vaginal dryness.

In a particular embodiment, the pharmaceutical or veterinary composition of the invention is administered orally, in particular when it is used in the treatment and/or prevention of burning mouth syndrome.

Oral dosage forms may be in solid or liquid form and may be tablets, capsules, syrups or solutions and may contain conventional excipients known in the prior art, such as binding agents, for example syrup, gum arabic, gelatine, sorbitol, gum tragacanth or polyvinylpyrrolidone; fillers, for example lactose, sugar, corn starch, calcium phosphate, sorbitol or glycine; lubricants for the preparation of tablets, for example magnesium stearate; disintegrants, for example starch, polyvinylpyrrolidone, sodium starch glycolate or microcrystalline cellulose; or pharmaceutically acceptable wetting agents such as sodium lauryl sulphate.

Said oral forms can be prepared by conventional methods of mixing, filling or tablet preparation. Repeated mixing operations can be used to distribute the active agent in all of these compositions using large amounts of fillers. Such operations are conventional in the prior art. The tablets can be prepared, for example, by wet or dry granulation and can optionally be coated according to methods that are well known in normal pharmaceutical practice, in particular with an enteric coating.

Parenteral dosage forms (e.g. intramuscular, intravenous, intraperitoneal, etc.) can comprise sterile solutions, suspensions or lyophilised products in the appropriate unit dosage form. Suitable excipients such as bulking agents, buffering agents or surfactants can be used.

The pharmaceutical or veterinary composition of the invention may contain a variable amount of compound of formula (I) within a broad range, but always in a therapeutically effective amount. The expression "therapeutically effective amount", as used herein, refers to the amount of compound of formula (I) that is sufficient to elicit a therapeutic effect in the patient receiving the pharmaceutical or veterinary composition, such as, for example, an increase in lachrymation, vaginal secretion or salivary secretion in said subject. In a particular embodiment, the pharmaceutical or veterinary composition of the invention contains between 0.1 mg and 2,000 mg, preferably between 0.5 mg and 500 mg and, even more preferably, between 1 mg and 200 mg of a compound of formula (I).

The dosage regimen will be determined by the doctor and clinical factors. The dosage of an active ingredient depends on many factors, including the physical characteristics of the patient (age, weight, etc.), the route of administration used, the severity of the disease, the particular compound used, etc. In general, the amount of a compound of formula (I) to be administered will depend on the relative efficacy of the compound chosen and the severity of the disorder treated. By way of illustration, a compound of formula (I) may be administered normally one or more times per day, for example 1, 2, 3 or 4 times per day, with a typical total daily dose in the range of 0.1 to 1,000 mg/kg body weight/day. In another embodiment, the pharmaceutical compositions provided by the present invention can be administered in doses of less than 10 mg per kg of body weight, preferably less than 5, 2, 1, 0.5, 0.1, 0.05, 0.01, 0.005, 0.001, 0.0005, 0.0001, 0.00005 or 0.00001 mg per kg of body weight.

In another embodiment, the pharmaceutical compositions provided are administered ophthalmically and comprise the compound of formula (I) as defined above and a pharmaceutically acceptable carrier for topical ophthalmic administration. In another embodiment, the above compositions are administered with a concentration of 0.000001 to 10.0% weight/volume, preferably between 0.00001 and 1.0%, and more preferably between 0.0001 and 0.5%, where the concentration is expressed as the weight of the compound of formula (I) in grams with respect to 100 ml total volume of the composition.

As stated above, the compounds of the invention are TRPM8 receptor agonists and as such can be used in different therapeutic applications. Therefore, another aspect of the invention relates to a compound of formula (I) as defined above for use in medicine or as a drug.

The term "TRPM8", as used in the present invention, refers to a transient receptor potential cation channel subfamily M member, also known as the cold and menthol receptor 1. The sequence of the TRPM8 protein in humans corresponds to the sequence with identifier Q7Z2W7 in the Uniprot database on Jul. 22, 2015.

Said term also includes functionally equivalent variants of TRPM8. The term "functionally equivalent variant of the TRPM8 protein" includes (i) variants of the TRPM8 protein in which one or more of the amino acid residues are substituted with a conserved or non-conserved amino acid residue (preferably a conserved amino acid residue), wherein said substituted amino acid residue may or may not be encoded by the genetic code, as well as (ii) variants comprising an insertion or deletion of one or more amino acids and which provide the same function as the TRPM8 protein, that is, to be able to allow the entry of sodium and calcium ions into the cell after activation.

The variants according to the invention preferably have a sequence identity with the amino acid sequence of TRPM8 of at least 50%, at least 60%, at least 70%, at least 80%, at least 90%, at least 91%, at least 92%, at least 93%, at least 94%, at least 95%, at least 96%, at least 97%, at least 98% or at least 99%. The degree of identity between the variants and the specific TRPM8 protein sequences defined above can be determined using algorithms and computer procedures that are generally known for a person skilled in the art. The identity between two amino acid sequences is preferably determined using the BLASTP algorithm (BLAST Manual, Altschul, S F et al, "*Basic Local Alignment Search Tool*", J. Mol. Biol. 1990, 215, 403-410).

Therefore, said term TRPM8 refers to the aforementioned protein of any animal, in particular a mammal and more particularly a human.

The term "TRPM8 receptor agonist", as used herein, refers to a compound that binds to the TRPM8 receptor and which, when bound, is capable of causing an increase in the activity of a TRPM8 channel, i.e. increasing the flow of sodium and calcium through the channel, causing a depolarisation of the cell. A wide variety of assays are available for detecting the activity of TRPM8 receptor agonists; illustratively, the methods based on fluorescence plate detection, "fluorometric imaging plate reader assay" [see Example 28] and calcium microscopy methods (Bodding et al, Cell Calcium 2007, 42, 618-628) can be cited, among others.

In a particular embodiment, the TRPM8 receptor agonists are specific agonists of said TRPM8 receptor. The term "specific agonist", as used herein, refers to the agonists of TRPM8 that activate TRPM8 without activating other channels of the same family or that activate TRPM8 with at least 50, 100, 1,000, 2,000 times more efficacy than another channel of the same family. The methods that can be used to measure the specificity of a TRPM8 agonist are similar to those described above for measuring the agonist activity of TRPM8 of a compound, such as electrophysiological methods, calcium microscopy methods, etc.

The compounds of formula (I) of the invention, since they are agonists of the TRPM8 channel, increase the stimulation of tear secretion by cold-sensitive fibres and are also useful in other related diseases that present with dry mucous surfaces. Thus, another aspect of the invention relates to a compound of formula (I), as defined above, for use in the treatment and/or prevention of xerophthalmia or dry eye syndrome, vaginal dryness or burning mouth syndrome. This aspect of the invention can also be formulated as a use of the compound of formula (I), as defined above, for the preparation of a drug for treating and/or preventing xerophthalmia or dry eye syndrome, vaginal dryness or burning mouth syndrome. The invention also relates to a method for the prevention and/or treatment of xerophthalmia or dry eye syndrome, vaginal dryness or burning mouth syndrome in a mammal, including a human being, comprising administration to said mammal of a therapeutically effective amount of the compound of formula (I), as defined above, together with one or more pharmaceutically acceptable excipients, adjuvants or vehicles.

As used herein, the term "xerophthalmia" or "dry eye syndrome" refers to a disease characterised by persistent dryness of the conjunctiva and opacity of the cornea. Xerophthalmia can have multiple causes, and it is more common among elderly persons. The following are some of the causes and diseases that can lead to xerophthalmia: vitamin A deficiency, Sjögren's syndrome, rheumatoid arthritis and other rheumatic diseases, chemical or thermal burns, drugs such as atenolol, chlorpheniramine, hydrochlorothiazide, isotretinoin, ketorolac, ketotifen, levocabastine, levofloxacin, oxybutynin, tolterodine, etc. In a particular embodiment, xerophthalmia is associated with vitamin A deficiency, Sjögren's syndrome, rheumatoid arthritis and other rheumatic diseases, chemical or thermal burns or drugs such as atenolol, chlorpheniramine, hydrochlorothiazide, isotretinoin, ketorolac, ketotifen, levocabastine, levofloxacin, oxybutynin or tolterodine.

The term "vaginal dryness", as used herein, refers to a decrease in the amount of fluids produced in the vagina. This dryness can cause discomfort, such as itching, irritation and a burning sensation in the genital area, as well as pain during sexual intercourse. This lack of lubrication can be brought on by organic or psychological causes. Among the organic causes, the most common is an insufficient amount of oestrogen (e.g. during menopause). Other causes of vaginal dryness include vaginitis, which is an inflammation of the vaginal tissues, or diabetes. In the case of women with diabetes, whose vaginal lubrication may be reduced, particularly in those with poor blood glucose control, this loss of lubrication can be associated with two complications: neuropathy, which can decrease the response to sexual stimulation, and damage to the blood vessels, which limits blood flow to the vaginal wall, decreasing the amount of lubricant flow. Another factor to consider is stress, which causes an increase in the release of cortisol into blood, which in turn produces an imbalance in the other hormones. Tobacco also interferes with oestrogen functions and, therefore, can decrease vaginal lubrication. Alcohol and marijuana can produce a similar effect. Certain hormonal medications, such as birth control pills or drugs used to treat breast, ovarian or uterine cancer, can cause vaginal dryness. Tricyclic antidepressants, some antiulcer drugs or certain antihypertensives may have a decrease in vaginal discharge as a side effect. Other drugs that might also cause this problem are antihistamines. In a particular embodiment, vaginal dryness is associated with an insufficient amount of oestrogen, diabetes, stress or consumption of alcohol, marijuana or drugs such as those used for the treatment of breast, ovarian or uterine cancer, tricyclic antidepressants, antiulcer drugs, antihypertensives or antihistamines.

The term "burning mouth syndrome", as used herein, refers to the disease termed stomatodynia. This disease is due to multiple causes. Inadequate consumption of certain vegetables or meat that provide iron, folic acid or vitamin B12, can contribute to deficiency anaemia, which contributes to this burning mouth syndrome. Likewise, some endocrine diseases, such as hypothyroidism or diabetes, or digestive diseases, such as gastroesophageal reflux, also contribute to burning mouth syndrome. Another aspect that influences the appearance of this disease is the chronic consumption of certain drugs such as beta-blockers, antihypertensives and antidiabetic drugs.

The compounds and compositions of this invention can be used with other drugs to provide combination therapy. The other drugs may be part of the same composition or may be provided as a separate composition for administration at the same time or at a different time.

Thus, another aspect of the invention relates to a compound of formula (I) as defined beforehand, for administration in combination with a second compound, for simultaneous, concurrent, separate or sequential use in the treatment and/or prevention of xerophthalmia or dry eye syndrome, vaginal dryness or burning mouth syndrome, wherein the second compound is a compound useful for the treatment of xerophthalmia or dry eye syndrome, vaginal dryness or burning mouth syndrome, respectively.

Another aspect of the invention relates to a single pharmaceutical or veterinary composition that comprises a therapeutically effective amount of a compound of formula (I) or formula (IA) as defined above, and of a second compound useful for the treatment of xerophthalmia or dry eye syndrome, vaginal dryness or burning mouth syndrome, together with one or more pharmaceutically or veterinarily acceptable excipients, adjuvants or vehicles.

Another aspect of the invention relates to a kit comprising a first pharmaceutical or veterinary composition comprising a therapeutically effective amount of a compound of formula (I) as defined above, together with one or more pharmaceutically or veterinarily acceptable excipients, adjuvants or vehicles, and a second pharmaceutical or veterinary composition comprising a therapeutically effective amount of a second compound, said second compound being useful for the treatment of xerophthalmia or dry eye syndrome, vaginal dryness or burning mouth syndrome, together with one or more pharmaceutically or veterinarily acceptable excipients, adjuvants or vehicles.

In a particular embodiment, the compound useful for the treatment of xerophthalmia or dry eye syndrome is selected from the group consisting of corticosteroids, vitamin A, pilocarpine, hypromellose solutions, carbomer gels, cyclosporin, lubricating ophthalmic drops containing glycerine, hydroxypropyl methylcellulose, hydroxymethyl cellulose, carboxymethyl cellulose, polyethylene glycol, polyvinyl alcohol, hyaluronic acid, castor oil and mineral oil.

In another particular embodiment, the compound useful for the treatment of vaginal dryness is selected from the group consisting of water-based lubricants, vitamin E, oestrogens, isoflavone aglycones, hyaluronic acid and selective oestrogen receptor modulators such as raloxifene.

In another particular embodiment, the compound useful for the treatment of burning mouth syndrome is selected from the group consisting of capsaicin, nystatin, fluconazole, anticonvulsants such as gabapentin, sedatives of the benzodiazepine family such as clonazepam, antidepressants, antiepileptics and anticonvulsants such as amitriptyline, carbamazepine, mexiletine, lamotrigine, phenytoin, N-phenylethyl amitriptyline, desipramine, gabapentin, nortriptyline, etc.

The term "treatment" includes both therapeutic treatment and prophylactic or preventive measures, wherein the object is to prevent or slow (reduce) an unwanted physiological change or disorder, such as dryness of the eyes, vagina or mouth. For the purposes of this invention, beneficial or desired clinical results include, without limitation, relief of symptoms, reduction of the extent of the disease, stabilised (specifically, not worsened) pathological state, retardation or delay of the progression of the disease, improvement or palliation of the pathological state and remission (both partial and total), both detectable and undetectable.

The term "prevention", as used herein, refers to preventing a disease or preventing or delaying the symptomatology thereof.

The term "patient", as used in the present invention, includes any mammal; non-limiting examples are domestic animals and livestock, primates and humans. The patient is preferably a human being, male or female, of any age or race.

Throughout the description and claims the word "comprises" and its variants do not intend to exclude other technical features, additives, components or steps. For a person skilled in the art, other subjects, advantages and characteristics of the invention will emerge partly from the description and partly from the practice of the invention. The following examples and drawings are provided by way of illustration, and are not intended to have a limiting effect on the present invention. The numerical signs relating to the drawings and placed between parentheses in a claim should only be used to improve understanding of the claim, and should not be interpreted as limiting the scope of protection of the claim. In addition, the present invention covers all possible combinations of particular and preferred embodiments indicated herein.

EXAMPLES

Figure 1:
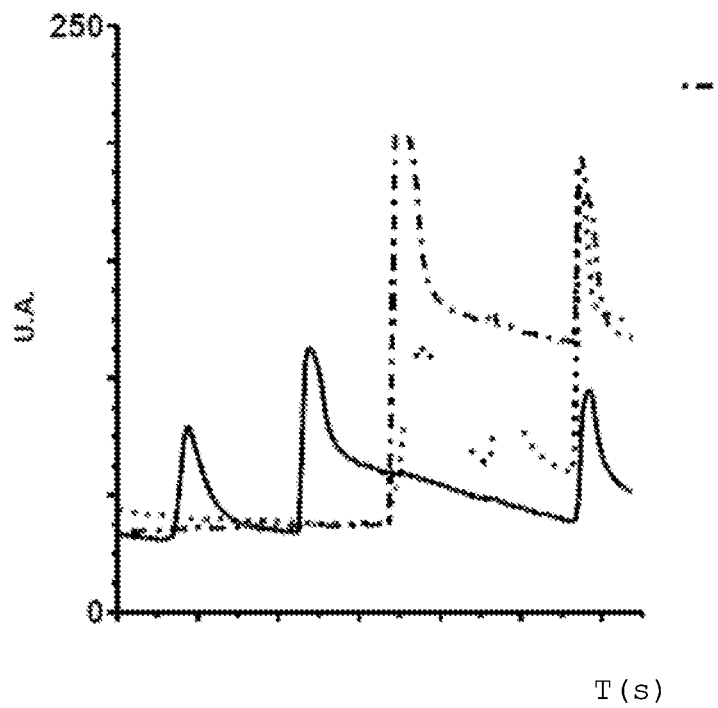
FIG. 1 illustrates the specificity of compound TZM-7 to activate TRPM8 (-) against TRPV1 (- . - .) and TRPA1 (- - -) measured by fluorescence (U.A.) as a function of time (s).

Example 1: General Procedure for Synthesising the Compounds of Formula (I)

One equivalent (eq) of (1R,2S,5R)-2-azido-1-isopropyl-4-methyl-cyclohexane [compound of formula (II)] and one equivalent (eq) of the corresponding alkyne [compound of formula (III)] were dissolved in a 1:1 water:tert-butanol solution. Sodium ascorbate (0.1 eq) of a 1 M solution in fresh prepared water was added to the mixture; then copper (II) sulphate pentahydrate (0.01 eq) was added. The resulting reaction was stirred at room temperature during 24 hours. The reaction mixture was diluted with water, cooled on ice, and the resulting precipitate was collected by filtration. When the addition of water did not result in precipitation of the triazole, the solvent was evaporated and purified by chromatography.

The compound of formula (II) was prepared according to the procedure published in Welschoff N. et al. Synthesis 2010, 3596-3601. The alkynes of formula (III) were purchased commercially from Sigma-Aldrich or prepared as described in Utsintong M. et al. Med. Chem. 2013, 9, 510-516.

The following is a description of the synthesis of some of the compounds of formula (I) and the spectroscopic characterisation thereof.

Example 2: (1-(((1R,2S,5R)-2-isopropyl-5-methylcyclohexyl)-1H-1,2,3-triazole-4-yl)methanol (Compound TZM-1)

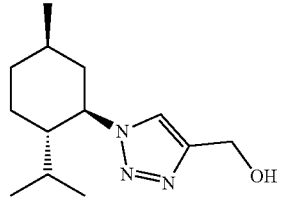 [SMILES: CC(C)[C@@H]1CC[C@@H](C)C[C@H]1n1cc(CO)nn1]

The compound of the title was synthesised as is described in the general procedure (Example 1), using the compound prop-2-yn-1-ol as alkyne. The product was obtained as a brown amorphous solid (84%).

$^1$H-NMR (300 MHz, CDCl$_3$) δ 7.51 (s, 1H), 4.79 (s, 2H), 4.40 (ddd, J=4.0, 11.5, 11.5 Hz, 1H), 3.02 (br s, 0H), 2.08 (br d, 1H), 1.63 (m, 5H), 1.10 (m, 3H), 0.95 (d, J=6.0 Hz, 3H), 0.82 (d, J=6.6 Hz, 3H), 0.75 (d, J=7.0 Hz, 3H). MS (ESI) m/z 260 (M+Na)$^+$.

Example 3: 1-((1R,2S,5R)-2-isopropyl-5-methylcyclohexyl)-4-(4-phenoxyphenyl)-1H-1,2,3-triazole (Compound TZM-2)

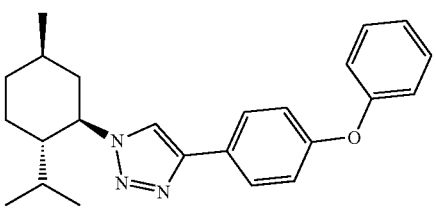 [SMILES: CC(C)[C@@H]1CC[C@@H](C)C[C@H]1n1cc(-c2ccc(Oc3ccccc3)cc2)nn1]

The compound of the title was synthesised as is described in the general procedure (Example 1), using the compound 1-ethynyl-4-phenoxy-benzene as alkyne. The product was obtained as a pale white solid (71%).

$^1$H-NMR (300 MHz, CDCl$_3$) δ 7.78 (d, J=8.2 Hz, 2H), 7.67 (s, 1H), 7.35 (t, J=7.6 Hz, 2H), 7.06 (m, 5H), 4.45 (ddd, J=4.0, 11.5, 11.5 Hz, 1H), 2.12 (br d, 1H), 1.82 (m, 3H), 1.54 (m, 2H), 1.17 (m, 3H), 0.99 (d, J=6.1 Hz, 3H), 0.82 (d, J=6.7 Hz, 3H), 0.77 (d, J=7.0 Hz, 3H). MS (ESI) m/z 399 (M+Na)$^+$.

Example 4: 1-((1R,2S,5R)-2-isopropyl-5-methylcyclohexyl)-4-phenyl-1H-1,2,3-triazole (Compound TZM-3)

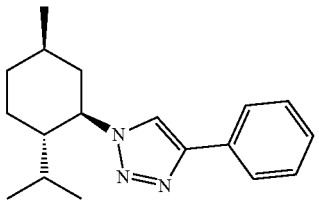 [SMILES: CC(C)[C@@H]1CC[C@@H](C)C[C@H]1n1cc(-c2ccccc2)nn1]

The compound of the title was synthesised as is described in the general procedure (Example 1), using the compound ethynyl-benzene as alkyne. The product was obtained as a yellowish solid (82%).

$^1$H-NMR (300 MHz, CDCl$_3$) δ 7.34 (d, J=8.2 Hz, 2H), 7.71 (s, 1H), 7.42 (t, J=7.3 Hz, 2H), 7.33 (m, 1H), 4.47 (ddd, J=4.0, 11.5, 11.5 Hz, 1H), 2.12 (br d, 1H), 1.81 (m, 3H), 1.58 (m, 2H), 1.20 (m, 3H), 0.98 (d, J=6.1 Hz, 3H), 0.85 (d, J=6.7 Hz, 3H), 0.77 (d, J=7.0 Hz, 3H). MS (ESI) m/z 306 (M+Na)$^+$.

Example 5: 1-((1R,2S,5R)-2-isopropyl-5-methylcyclohexyl)-4-(4-methoxyphenyl)-1H-1,2,3-triazole (Compound TZM-4)

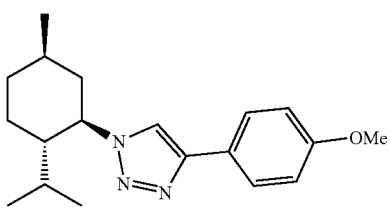 [SMILES: COc1ccc(-c2cn([C@@H]3C[C@H](C)CC[C@H]3C(C)C)nn2)cc1]

The compound of the title was synthesised as is described in the general procedure (Example 1), using the compound 1-ethynyl-4-methoxy-benzene as alkyne. The product was obtained as a slightly yellow solid (65%).

$^1$H-NMR (300 MHz, CDCl$_3$+CD$_3$OD) δ 7.73 (d, J=8.8 Hz, 2H, AA'XX'), 7.63 (s, 1H), 7.93 (d, J=8.8 Hz, 2H, AA'XX'), 4.44 (ddd, J=4.0, 11.5, 11.5 Hz, 1H), 3.79 (s, 3H), 2.09 (br d, 1H), 1.80 (m, 3H), 1.54 (m, 2H), 1.18 (m, 3H), 0.96 (d, J=6.1 Hz, 3H), 0.820 (d, J=6.7 Hz, 3H), 0.71 (d, J=7.0 Hz, 3H). MS (ESI) m/z 336 (M+Na)$^+$.

Example 6: 4-([1,1'-biphenyl]-4-yl)-1-((1R,2S,5R)-2-isopropyl-5-methylcyclohexyl)-1H-1,2,3-triazole (Compound TZM-5)

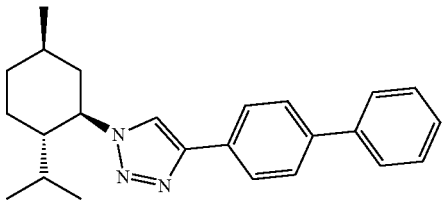 [SMILES: CC(C)[C@@H]1CC[C@@H](C)C[C@H]1n1cc(-c2ccc(-c3ccccc3)cc2)nn1]

The compound of the title was synthesised as is described in the general procedure (Example 1), using the compound 4-ethynyl-biphenyl as alkyne. The product was obtained as a white solid (71%).

$^1$H-NMR (300 MHz, CDCl$_3$) δ 7.91 (d, J=8.2 Hz, 2H), 7.58 (m, 4H), 7.43 (m, 4H), 4.48 (ddd, J=4.0, 11.5, 11.5 Hz, 1H), 2.16 (br d, 1H), 1.83 (m, 3H), 1.67 (m, 2H), 1.08 (m, 3H), 0.97 (d, J=6.1 Hz, 3H), 0.83 (d, J=6.7 Hz, 3H), 0.78 (d, J=7.0 Hz, 3H). MS (ESI) m/z 383 (M+Na)$^+$.

Example 7: 1-(1-((1R,2S,5R)-2-isopropyl-5-methylcyclohexyl)-1H-1,2,3-triazole-4-yl)cyclohexan-1-ol (Compound TZM-6)

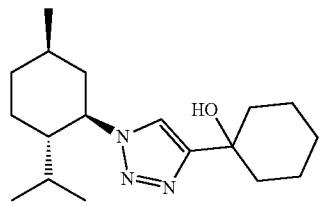 [SMILES: CC(C)[C@@H]1CC[C@@H](C)C[C@H]1n1cc(C2(O)CCCCC2)nn1]

The compound of the title was synthesised as is described in the general procedure (Example 1), using the compound 1-ethynyl-cyclohexanol as alkyne. The product was obtained as a slightly yellow solid (64%).

$^1$H-NMR (300 MHz, CDCl$_3$) δ 7.37 (s, 1H), 4.41 (ddd, J=4.0, 11.5, 11.5 Hz, 1H), 2.46 (br s, 1H), 1.73 (m, 13H), 1.06 (m, 5H), 0.97 (d, J=6.1 Hz, 3H), 0.89 (d, J=6.7 Hz, 3H), 0.65 (d, J=7.0 Hz, 3H). MS (ESI) m/z 328 (M+Na)$^+$.

Example 8: 4-(3,5-dimethoxyphenyl)-1-((1R,2S,5R)-2-isopropyl-5-methylcyclohexyl)-1H-1,2,3-triazole (Compound TZM-7)

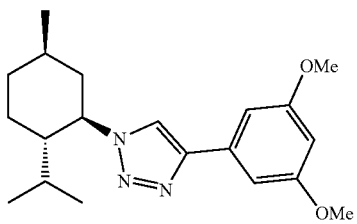 [SMILES: COc1cc(OC)cc(-c2cn([C@@H]3C[C@H](C)CC[C@H]3C(C)C)nn2)c1]

The compound of the title was synthesised as is described in the general procedure (Example 1), using the compound 1-ethynyl-3,5-dimethoxy-benzene as alkyne. The product was obtained as a white solid (70%).

$^1$H-NMR (300 MHz, CDCl$_3$) δ 7.72 (s, 1H), 7.00 (d, J=2.16 Hz, 2H), 6.40 (t, J=2.16 Hz, 1H), 4.41 (ddd, J=4.0, 11.5, 11.5 Hz, 1H), 3.80 (br s, 6H), 2.07 (br d, 1H), 1.76 (m, 3H), 1.54 (m, 2H), 1.19 (m, 3H), 0.91 (d, J=6.1 Hz, 3H), 0.77 (d, J=6.7 Hz, 3H), 0.73 (d, J=7.0 Hz, 3H). MS (ESI) m/z 366 (M+Na)$^+$.

Example 9: 1-((1R,2S,5R)-2-isopropyl-5-methylcyclohexyl)-4-(naphthalene-1-yl)-1H-1,2,3-triazole (Compound TZM-8)

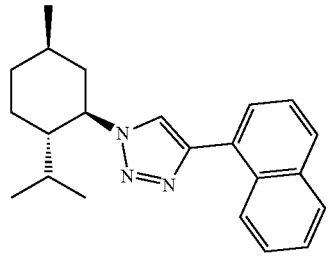 [SMILES: CC(C)[C@@H]1CC[C@@H](C)C[C@H]1n1cc(-c2cccc3ccccc23)nn1]

The compound of the title was synthesised as is described in the general procedure (Example 1), using the compound 1-ethynyl-naphthalene as alkyne. The product was obtained as a yellow solid (54%).

$^1$H-NMR (300 MHz, CDCl$_3$) δ 8.41 (m, 1H), 8.40 (m, 2H), 7.83 (m, 3H), 7.52 (m, 2H), 4.53 (ddd, J=4.0, 11.5, 11.5 Hz, 1H), 2.20 (br d, 1H), 1.85 (m, 3H), 1.63 (m, 2H), 1.25 (m, 3H), 1.00 (d, J=6.1 Hz, 3H), 0.87 (d, J=6.7 Hz, 3H), 0.82 (d, J=7.0 Hz, 3H). MS (ESI) m/z 356 (M+Na)$^+$.

Example 10: 2-(1-((1R,2S,5R)-2-isopropyl-5-methylcyclohexyl)-1H-1,2,3-triazole-4-yl)pyridine (Compound TZM-9)

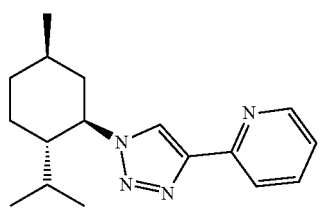 [SMILES: CC(C)[C@@H]1CC[C@@H](C)C[C@H]1n1cc(-c2ccccn2)nn1]

The compound of the title was synthesised as is described in the general procedure (Example 1), using the compound 2-ethynyl-pyridine as alkyne. The product was obtained as a brown solid (62%).

$^1$H-NMR (300 MHz, CDCl$_3$) δ 8.58 (br s, 2H), 8.19 (br s, 2H), 7.79 (br s, 1H), 4.53 (m, 1H), 2.12 (br d, 1H), 1.84 (m, 3H), 1.58 (m, 2H), 1.25 (m, 3H), 1.00 (d, J=6.1 Hz, 3H), 0.87 (d, J=6.7 Hz, 3H), 0.82 (d, J=7.0 Hz, 3H. MS (ESI) m/z 307 (M+Na)$^+$.

Example 11: 1-((1R,2S,5R)-2-isopropyl-5-methylcyclohexyl)-4-phenethyl-1H-1,2,3-triazole (Compound TZM-10)

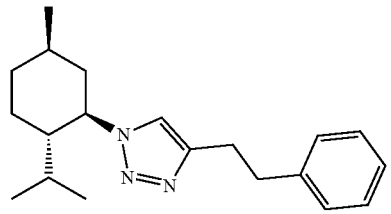 [SMILES: CC(C)[C@@H]1CC[C@@H](C)C[C@H]1n1cc(CCc2ccccc2)nn1]

The compound of the title was synthesised as is described in the general procedure (Example 1), using the compound but-3-ynyl-benzene as alkyne. The product was obtained as a brown solid (52%).

$^1$H-NMR (300 MHz, CDCl$_3$) δ 7.14 (m, 6H), 4.35 (ddd, J=4.0, 11.5, 11.5 Hz, 1H), 3.01 (br s, 4H), 1.97 (br d, 1H), 1.66 (m, 3H), 1.43 (m, 2H), 1.04 (m, 3H), 0.93 (d, J=6.1 Hz, 3H), 0.77 (d, J=6.7 Hz, 3H), 0.69 (d, J=7.0 Hz, 3H). MS (ESI) m/z 269 (M+Na)$^+$.

Example 12: (3,4-dimethoxyphenyl) (1-((1R,2S, 5R)-2-isopropyl-5-methylcyclohexyl)-1H-1,2,3-triazole-4-yl)methanone (Compound TZM-11)

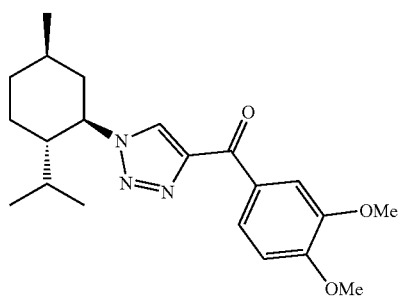 [SMILES: COc1ccc(C(=O)c2cn([C@@H]3C[C@H](C)CC[C@H]3C(C)C)nn2)cc1OC]

The compound of the title was synthesised as is described in the general procedure (Example 1), using the compound 1-(3,4-dimethoxy-phenyl)-propynone as alkyne. The product was obtained as a white solid (70%).

$^1$H-NMR (300 MHz, CDCl$_3$) δ 8.40 (dd, J=1.8, 8.0 Hz, 1H), 8.21 (s, 1H), 8.06 (d, J=1.8 Hz, 1H), 6.96 (d, J=8.0 Hz, 1H), 4.49 (ddd, J=4.0, 11.5, 11.5 Hz, 1H), 3.97 (br d, 6H), 2.13 (br d, 1H), 1.78 (m, 3H), 1.55 (m, 2H), 1.17 (m, 3H), 0.98 (d, J=6.1 Hz, 3H), 0.82 (d, J=6.7 Hz, 3H), 0.78 (d, J=7.0 Hz, 3H). MS (ESI) m/z 394 (M+Na)$^+$.

Example 13: (3-fluorophenyl) (1-((1R,2S,5R)-2-isopropyl-5-methylcyclohexyl)-1H-1,2,3-triazole-4-yl)methanone (Compound TZM-12)

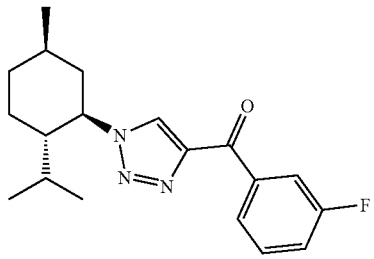 [SMILES: CC(C)[C@@H]1CC[C@@H](C)C[C@H]1n1cc(C(=O)c2cccc(F)c2)nn1]

The compound of the title was synthesised as is described in the general procedure (Example 1), using the compound 1-(3-fluoro-phenyl)-propynone as alkyne. The product was obtained as a yellowish oil (58%).

$^1$H-NMR (300 MHz, CDCl$_3$) δ 8.31 (d, J=7.9 Hz, 1H), 8.32 (s, 1H), 8.18 (br d), 7.46 (m, 1H), 7.27 (m, 1H), 4.50 (ddd, J=4.0, 11.5, 11.5 Hz, 1H), 2.11 (br d, 1H), 1.78 (m, 3H), 1.59 (m, 2H), 1.15 (m, 3H), 0.96 (d, J=6.1 Hz, 3H), 0.82 (d, J=6.7 Hz, 3H), 0.75 (d, J=7.0 Hz, 3H). MS (ESI) m/z 352 (M+Na)$^+$.

Example 14: (1-((1R,2S,5R)-2-isopropyl-5-methyl-cyclohexyl)-1H-1,2,3-triazole-4-yl) (4-phenoxyphenyl)methanone (Compound TZM-13)

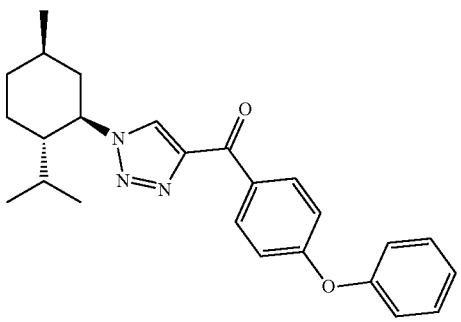 [SMILES: CC(C)[C@@H]1CC[C@@H](C)C[C@H]1n1cc(C(=O)c2ccc(Oc3ccccc3)cc2)nn1]

The compound of the title was synthesised as is described in the general procedure (Example 1), using the compound 1-(4-phenoxy-phenyl)-propynone as alkyne. The product was obtained as a yellowish oil (45%).

$^1$H-NMR (300 MHz, CDCl$_3$) δ 8.51 (dd, J=8.9, 1.9 Hz, 2H), 8.25 (s, 1H), 7.36 (btt, 2H), 7.13 (br t, 1H), 7.08 (m, 4H), 4.49 (ddd, J=4.0, 11.5, 11.5 Hz, 1H), 2.10 (br d, 1H), 1.79 (m, 3H), 1.55 (m, 2H), 1.21 (m, 3H), 0.93 (d, J=6.1 Hz, 3H), 0.79 (d, J=6.7 Hz, 20 3H), 0.73 (d, J=7.0 Hz, 3H). MS (ESI) m/z 427 (M+Na)$^+$.

Example 15: (2,4-dimethoxyphenyl) (1-((1R,2S,5R)-2-isopropyl-5-methylcyclohexyl)-1H-1,2,3-triazole-4-yl)methanone (Compound TZM-14)

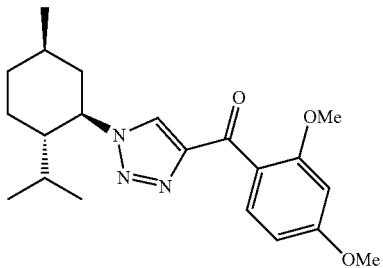 [SMILES: COc1ccc(C(=O)c2cn([C@@H]3C[C@H](C)CC[C@H]3C(C)C)nn2)c(OC)c1]

The compound of the title was synthesised as is described in the general procedure (Example 1), using the compound 1-(2,4-dimethoxy-phenyl)-propynone as alkyne. The product was obtained as a pale yellow solid (35%).

$^1$H-NMR (300 MHz, CDCl$_3$) δ 8.10 (s, 1H), 7.82 (d, J=8.3 Hz, 1H), 6.51 (m, 2H), 4.46 (ddd, J=4.0, 11.5, 11.5 Hz, 1H), 3.85 (s, 3H), 3.78 (s, 3H), 2.08 (br d, 1H), 1.82 (m, 3H), 1.53 (m, 2H), 1.18 (m, 3H), 0.96 (d, J=6.1 Hz, 3H), 0.82 (d, J=6.7 Hz, 3H), 0.76 (d, J=7.0 Hz, 3H). MS (ESI) m/z 394 (M+Na)$^+$.

Example 16: (1-((1R,2S,5R)-2-isopropyl-5-methyl-cyclohexyl)-1H-1,2,3-triazole-4-yl) (2-methoxyphenyl)methanone (Compound TZM-15)

The compound of the title was synthesised as is described in the general procedure (Example 1), using the compound 1-(2-methoxy-phenyl)-propynone as alkyne. The product was obtained as a white solid (47%).

$^1$H-NMR (300 MHz, CDCl$_3$) δ 8.09 (s, 1H), 7.60 (d, J=7.6 Hz, 1H), 7.46 (br t, 1H), 7.03 (d, 1H overlapped), 7.00 (brt, 1H, overlapped), 4.46 (ddd, J=4.0, 11.5, 11.5 Hz, 1H), 3.77 (s, 3H), 2.09 (br d, 1H), 1.77 (m, 3H), 1.54 (m, 2H), 1.14 (m, 3H), 0.93 (d, J=6.1 Hz, 3H), 0.80 (d, J=6.7 Hz, 3H), 0.73 (d, J=7.0 Hz, 3H). MS (ESI) m/z 364 (M+Na)$^+$.

Example 17: (3,5-dimethoxyphenyl) (1-((1R,2S,5R)-2-isopropyl-5-methylcyclohexyl)-1H-1,2,3-triazole-4-yl)methanone (Compound TZM-16)

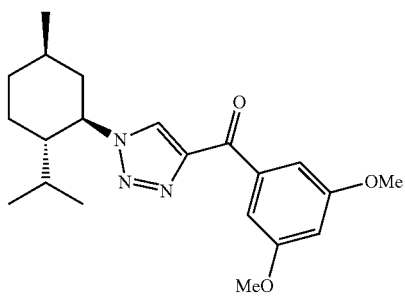 [SMILES: COc1cc(OC)cc(C(=O)c2cn([C@@H]3C[C@H](C)CC[C@H]3C(C)C)nn2)c1]

The compound of the title was synthesised as is described in the general procedure (Example 1), using the compound 1-(3,5-dimethoxy-phenyl)-propynone as alkyne. The product was obtained as a colourless oil (55%).

¹H-NMR (300 MHz, CDCl₃) δ 8.22 (s, 1H), 7.65 (d, J=1.86 Hz, 2H), 6.68 (t, J=1.86, 1H), 4.48 (ddd, J=4.0, 11.5, 11.5 Hz, 1H), 3.83 (s, 6H), 2.09 (br d, 1H), 1.80 (m, 3H), 1.56 (m, 2H), 1.17 (m, 3H), 0.82 (d, J=6.1 Hz, 3H), 0.80 (d, J=6.7 Hz, 3H), 0.74 (d, J=7.0 Hz, 3H). MS (ESI) m/z 394 (M+Na)⁺.

Example 18: [1,1'-biphenyl]-4-yl(1-((1R,2S,5R)-2-isopropyl-5-methylcyclohexyl)-1H-1,2,3-triazole-4-yl)methanone (Compound TZM-17)

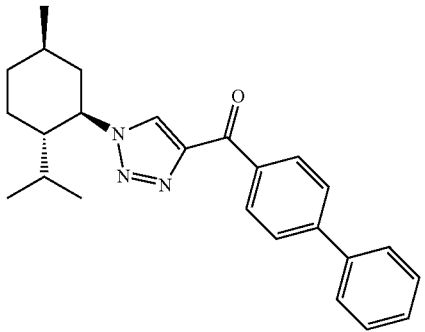 [SMILES: CC(C)[C@@H]1CC[C@@H](C)C[C@H]1n1cc(C(=O)c2ccc(-c3ccccc3)cc2)nn1]

The compound of the title was synthesised as is described in the general procedure (Example 1), using the compound 1-biphenyl-4-yl-propynone as alkyne. The product was obtained as a yellow oil (35%).

¹H-NMR (300 MHz, CDCl₃) δ 8.57 (d, J=8.3 Hz, 2H), 8.25 (s, 1H), 7.74 (d, J=8.3 Hz, 2H), 7.66 (d, J=7.1 Hz, 2H), 7.47 (m, 3H), 4.53 (ddd, J=4.0, 11.5, 11.5 Hz, 1H), 2.15 (br d, 1H), 1.82 (m, 3H), 1.60 (m, 2H), 1.22 (m, 3H), 1.00 (d, J=6.1 Hz, 3H), 0.84 (d, J=6.7 Hz, 3H), 0.78 (d, J=7.0 Hz, 3H). MS (ESI) m/z 411 (M+Na)⁺.

Example 19: (1-((1R,2S,5R)-2-isopropyl-5-methylcyclohexyl)-1H-1,2,3-triazole-4-yl) (4-methoxyphenyl)methanone (Compound TZM-18)

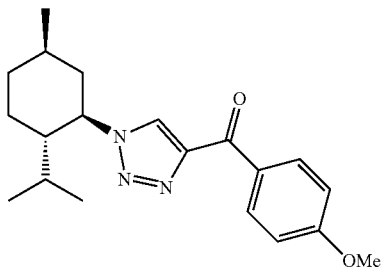 [SMILES: COc1ccc(C(=O)c2cn([C@@H]3C[C@H](C)CC[C@H]3C(C)C)nn2)cc1]

The compound of the title was synthesised as is described in the general procedure (Example 1), using the compound 1-(4-methoxy-phenyl)-propynone as alkyne. The product was obtained as a yellow solid (43%).

¹H-NMR (300 MHz, CDCl₃) δ 8.55 (d, J=8.8 Hz, 2H, AA'XX'), 8.21 (s, 1H), 6.98 (d, J=8.8 Hz, 2H, AA'XX'), 4.49 (ddd, J=4.0, 11.5, 11.5 Hz, 1H), 3.87 (s, 3H), 2.11 (br d, 1H), 1.80 (m, 3H), 1.54 (m, 2H), 1.20 (m, 3H), 0.96 (d, J=6.1 Hz, 3H), 0.80 (d, J=6.7 Hz, 3H), 0.74 (d, J=7.0 Hz, 3H). MS (ESI) m/z 364 (M+Na)⁺.

Example 20: (1-((1R,2S,5R)-2-isopropyl-5-methylcyclohexyl)-1H-1,2,3-triazole-4-yl) (3-methoxyphenyl)methanone (Compound TZM-19)

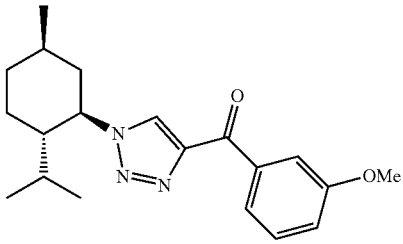 [SMILES: COc1cccc(C(=O)c2cn([C@@H]3C[C@H](C)CC[C@H]3C(C)C)nn2)c1]

The compound of the title was synthesised as is described in the general procedure (Example 1), using the compound 1-(3-methoxy-phenyl)-propynone as alkyne. The product was obtained as a yellow oil (44%).

¹H-NMR (300 MHz, CDCl₃) δ 8.22 (brs, 1H), 8.11 (brd, 1H), 7.96 (brs, 1H), 7.41 (m, 1H), 7.14 (m, 1H), 4.50 (ddd, J=4.0, 11.5, 11.5 Hz, 1H), 3.87 (s, 3H), 2.09 (br d, 1H), 1.83 (m, 3H), 1.58 (m, 2H), 1.09 (m, 3H), 0.96 (d, J=6.1 Hz, 3H), 0.81 (d, J=6.7 Hz, 3H), 0.75 (d, J=7.0 Hz, 3H). MS (ESI) m/z 364 (M+Na)⁺.

Example 21: (4-chlorophenyl) (1-((1R,2S,5R)-2-isopropyl-5-methylcyclohexyl)-1H-1,2,3-triazole-4-yl)methanone (Compound TZM-20)

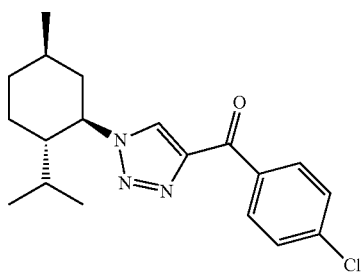 [SMILES: CC(C)[C@@H]1CC[C@@H](C)C[C@H]1n1cc(C(=O)c2ccc(Cl)cc2)nn1]

The compound of the title was synthesised as is described in the general procedure (Example 1), using the compound 1-(4-chloro-phenyl)-propynone as alkyne. The product was obtained as a white solid (65%).

¹H-NMR (300 MHz, CDCl₃) δ 8.46 (d, J=8.6 Hz, 2H, AA'XX'), 8.26 (s, 1H), 7.46 (d, J=8.6 Hz, 2H, AA'XX'), 4.50 (ddd, J=4.0, 11.5, 11.5 Hz, 1H), 2.10 (br d, 1H), 1.77 (m, 3H), 1.56 (m, 2H), 1.13 (m, 3H), 0.97 (d, J=6.1 Hz, 3H), 0.82 (d, J=6.7 Hz, 3H), 0.74 (d, J=7.0 Hz, 3H). MS (ESI) m/z 369 (M+Na)⁺.

Example 22: 9-(1-((1R,2S,5S)-2-isopropyl-5-methylcyclohexyl)-1H-1,2,3-triazole-4-yl)-nonanoic acid (Compound TZM-21)

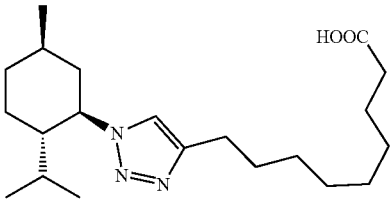 [SMILES: CC(C)[C@@H]1CC[C@@H](C)C[C@H]1n1cc(CCCCCCCCC(=O)O)nn1]

The compound of the title was synthesised as is described in the general procedure (Example 1), using the compound 10-undecyonic acid as alkyne. The product was obtained as a white solid (34%).

$^1$H-NMR (300 MHz, CDCl$_3$) δ 7.21 (s, 1H), 4.36 (ddd, J=4.0, 11.5, 11.5 Hz, 1H), 2.70 (t, J=7.4 Hz, 2H), 2.33 (t, J=7.4 Hz, 2H), 2.07 (br d, 1H), 1.35 (m, 21H), 0.95 (d, J=6.1 Hz, 3H), 0.79 (d, J=6.7 Hz, 3H), 0.72 (d, J=7.0 Hz, 3H). MS (ESI) m/z 387 (M+Na)$^+$.

Example 23: 5-(1-((1R,2S,5S)-2-isopropyl-5-methylcyclohexyl)-1H-1,2,3-triazole-4-yl)pentanenitrile (Compound TZM-22)

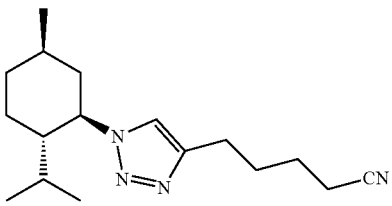 [SMILES: CC(C)[C@@H]1CC[C@@H](C)C[C@H]1n1cc(CCCCC#N)nn1]

The compound of the title was synthesised as is described in the general procedure (Example 1), using the compound hept-6-ene-nitrile as alkyne. The product was obtained as a colourless oil (57%).

$^1$H-NMR (300 MHz, CDCl$_3$) δ 7.26 (s, 1H), 4.34 (ddd, J=4.0, 11.5, 11.5 Hz, 1H), 2.71 (t, J=6.4 Hz, 2H), 2.33 (t, J=6.7 Hz, 2H), 1.98 (br d, 1H), 1.65 (m, 9H), 1.05 (m, 3H), 0.89 (d, J=6.1 Hz, 3H), 0.75 (d, J=6.7 Hz, 3H), 0.67 (d, J=7.0 Hz, 3H). MS (ESI) m/z 311 (M+Na)$^+$.

Example 24

3-[1-((1R,2S,5R)-2-isopropyl-5-methylcyclohexyl)-1H-1,2,3-triazole-4-yl]phenol (Compound TZM-23)

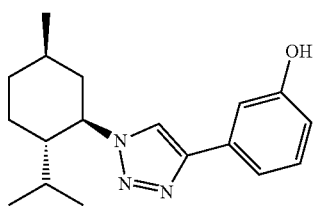 [SMILES: CC(C)[C@@H]1CC[C@@H](C)C[C@H]1n1cc(-c2cccc(O)c2)nn1]

The compound of the title was synthesised as is described in the general procedure (Example 1), using the compound 3-ethynyl-phenol as alkyne. The product was obtained as a yellow oil (68%).

$^1$H-NMR (300 MHz, CDCl$_3$) δ 7.67 (br d, 2H), 7.26 (m, 2H), 6.91 (d, J=7.9 Hz, 1H), 4.41 (ddd, J=4.0, 11.5, 11.5 Hz, 1H), 2.05 (br d, 1H), 1.79 (m, 3H), 1.53 (m, 2H), 1.23 (m, 3H), 0.91 (d, J=6.1 Hz, 3H), 0.77 (d, J=6.7 Hz, 3H), 0.71 (d, J=7.0 Hz, 3H). MS (ESI) m/z 322 (M+Na)$^+$.

Example 25: 1-((1R,2S,5R)-2-isopropyl-5-methylcyclohexyl)-4-(3-methoxyphenyl)-1H-1,2,3-triazole (Compound TZM-24)

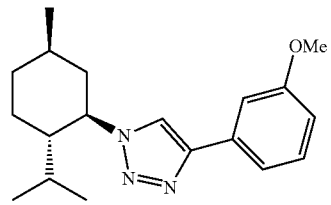 [SMILES: COc1cccc(-c2cn([C@@H]3C[C@H](C)CC[C@H]3C(C)C)nn2)c1]

The compound of the title was synthesised as is described in the general procedure (Example 1), using the compound 1-ethynyl-3-methoxy-phenol as alkyne. The product was obtained as a white solid (45%).

$^1$H-NMR (300 MHz, CDCl$_3$) δ 7.72 (s, 1H), 7.47 (s, 1H), 7.32 (m, 2H), 6.85 (dd, J=7.9 I 2.1, Hz, 1H), 4.43 (ddd, J=4.0, 11.5, 11.5 Hz, 1H), 3.85 (s, 3H), 2.09 (br d, 1H), 1.75 (m, 3H), 1.55 (m, 2H), 1.18 (m, 3H), 0.94 (d, J=6.1 Hz, 3H), 0.80 (d, J=6.7 Hz, 3H), 0.75 (d, J=7.0 Hz, 3H). MS (ESI) m/z 336 (M+Na)$^+$.

Example 26: 1-((1R,2S,5R)-2-isopropyl-5-methylcyclohexyl)-4-(methoxymethyl)-1H-1,2,3-triazole (Compound TZM-25)

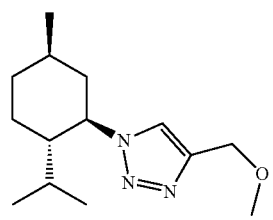 [SMILES: COCc1cn([C@@H]2C[C@H](C)CC[C@H]2C(C)C)nn1]

The compound of the title was synthesised as is described in the general procedure (Example 1), using the compound 3-methoxy-propyne as alkyne. The product was obtained as a yellow oil (52%).

$^1$H-NMR (300 MHz, CDCl$_3$) δ 7.46 (s, 1H), 4.55 (s, 2H), 4.37 (ddd, J=4.0, 11.5, 11.5 Hz, 1H), 3.38 (s, 3H), 2.03 (brd, 1H), 1.75 (m, 3H), 1.48 (m, 2H), 1.11 (m, 3H), 0.90 (d, J=6.1 Hz, 3H), 0.77 (d, J=6.7 Hz, 3H), 0.70 (d, J=7.0 Hz, 3H). MS (ESI) m/z 274 (M+Na)$^+$.

Example 27: (3,4-dimethoxyphenyl) (1-((1R,2S, 5R)-2-isopropyl-5-methylcyclohexyl)-1H-1,2,3-triazole-4-yl)methanol (Compound TZM-26)

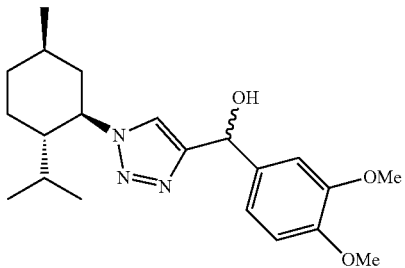 [SMILES: COc1ccc(C(O)c2cn([C@@H]3C[C@H](C)CC[C@H]3C(C)C)nn2)cc1OC]

The compound of the title was synthesised as is described in the general procedure (Example 1), using the compound 1-(3,4-dimethoxy-phenyl)-prop-2-yn-1-ol as alkyne. The product was obtained as a yellow oil (49%).

$^1$H-NMR (300 MHz, CDCl$_3$) δ 7.15 (br d, 1H), 6.96 (m, 2H), 6.82 (d, J=7.9 Hz, 1H), 5.94 (d, J=3.3 Hz, 1H), 4.33 (ddd, J=4.0, 11.5, 11.5 Hz, 1H), 3.81 (s, 3H), 3.80 (s, 3H), 1.97 (br d, 1H), 1.63 (m, 3H), 1.22 (m, 2H), 1.05 (m, 3H), 0.91 (d, J=6.1 Hz, 3H), 0.76 (d, J=6.7 Hz, 3H), 0.68 (d, J=7.0 Hz, 3H). MS (ESI) m/z 396 (M+Na)$^+$.

Example 28: In Vitro Tests of the Compounds TZM-1-TZM-26 on TRPM8

The activity of the compounds TZM-1-TZM-26 on TRPM8 was determined and, subsequently, the EC50 of some compounds that displayed high activity for activating the TRPM8 channel and their specificity for TRPM8 compared with other receptors of the same family was determined.

A) Determining the Activity of TZM-1-TZM-26 on TRPM8

The measurements of the efficacy of the compounds TZM-1-TZM-26 were carried out using the Chinese hamster ovary (CHO) cell line, which stably expresses the TRPM8 protein. The cells were cultured in monolayer in EMEM medium (Earle's minimum essential medium with Earle's salts, Invitrogen) supplemented with 10% foetal bovine serum (FBS), 2 mM L-glutamine, 1% penicillin-streptomycin solution and 0.4 µg/mL of the Geneticin antibiotic (Sigma) and kept at 37° C. in a humidified atmosphere with 5% of CO$_2$. Ca$^{2+}$ fluorimetry assays were carried out in order to determine the efficacy of the compounds on the TRPM8 channels. The cells were seeded in 96-well plates with a density of 25,000 cells per well. Three days after seeding, the medium was removed and 100 µl of the Fluo-4NW fluorescent probe from Invitrogen was added with a concentration of 5 µM in the presence of 0.02% pluronic acid; after 60 minutes of incubation at 37° C. in a humidified atmosphere with 5% of CO$_2$, the fluorescence was measured in a microplate reader (POLARstar Omega) with a configuration of 485 nm for the excitation and 520 nm for the emission, during 20 cycles. During the first 3 cycles, the basal fluorescence was measured and then 1 µl of the various compounds (TZM-1-TZM-26) was added at a final concentration of 10 µM; after seven fluorescence measurement cycles, 10 µl of menthol was added to all the wells in order to obtain a final concentration of 100 µM. In the wells that were used as negative controls, 1 µl of AMTB [N-(3-aminopropyl)-2-[(3-methylphenyl)methoxy]-N-(2-thienylmethyl)benzamide] was added to obtain a final concentration of 10 µM, to block the TRPM8 channels. Table 2 shows the results of the activity of the compounds TZM-1-TZM-26 on TRPM8.

TABLE 2

| Compounds | % activation of TRPM8 at 10 µM |
|---|---|
| Menthol | 100.56 ± 1.66 |
| TZM-1 | 45.47 ± 11.21 |
| TZM-2 | 55.64 ± 26.24 |
| TZM-3 | 51.56 ± 13.98 |
| TZM-4 | 85.06 ± 32.99 |
| TZM-5 | 50.14 ± 8.25 |
| TZM-6 | 45.13 ± 16.88 |
| TZM-7 | 78.54 ± 30.58 |
| TZM-8 | 56.46 ± 29.74 |
| TZM-9 | 59.08 ± 30.41 |
| TZM-10 | 45.00 ± 23.41 |
| TZM-11 | 53.54 ± 13.38 |
| TZM-12 | 57.93 ± 8.57 |
| TZM-13 | 46.47 ± 6.57 |
| TZM-14 | 43.76 ± 4.22 |
| TZM-15 | 50.48 ± 4.83 |
| TZM-16 | 44.49 ± 5.59 |
| TZM-17 | 41.98 ± 4.53 |
| TZM-18 | 44.63 ± 5.62 |
| TZM-19 | 40.78 ± 9.01 |
| TZM-20 | 66.90 ± 17.52 |
| TZM-21 | 54.02 ± 14.44 |
| TZM-22 | 57.33 ± 15.21 |
| TZM-23 | 51.21 ± 16.11 |
| TZM-24 | 37.84 ± 5.49 |
| TZM-25 | 45.07 ± 18.56 |
| TZM-26 | 50.86 ± 17.22 |

A) Measuring the EC50

Next, some of the components with high capacity to activate the TRPM8 channels will be selected and their EC50 (half maximum effective concentration) will be measured, using the same assay described above although, in this case, the cells were exposed to different concentrations of the selected compounds (in µM: 0.1, 1, 10, and 100) to generate the dose-response curve. The amplitudes of the Ca$^{2+}$ increases, caused by the stimulation of the cells with the compounds, were measured by subtracting the basal fluorescence signal (mean intensity obtained before adding the compound) from the fluorescence peak obtained after applying the compounds. The obtained results were adjusted to a sigmoid function using the software suite of the Graph-Pad Prism computer program. The results are shown in Table 3.

TABLE 3

| Compound | EC50 (µM) |
|---|---|
| Menthol | 196 ± 22 |
| TZM-4 | 3.47 ± 1.34 |
| TZM-7 | 2.91 ± 0.21 |
| TZM-9 | 6.23 ± 3.18 |
| TZM-10 | 3.84 ± 2.36 |
| TZM-11 | 9.84 ± 3.29 |

A) Determining the Specificity of the TZM-7 Compound to Activate TRPM8

Neurons obtained from a mouse dorsal root ganglion (DRG) were used to determine the specificity of the TZM-7 compound. These cells constitutively express the TRPM8, TRPV1 and TRPA1 channels, among others (the TRPV1 and TRPA1 channels are channels of the same family as the TRPM8 channel and are permeable to calcium). The intracellular Ca$^{2+}$ concentration was measured using fluorescence microscopy in order to view the activity of these channels. The cells were seeded with a density of 250,000 cells/well on round glass cover slips (18 mm diameter, thickness 0) in 12-well plates (Costar) and cultured in Pure-EMEM during 3 days immediately before the Ca$^{2+}$ experiments. The DRG neurons thus seeded were loaded with the acetoxymethyl ester of the fluorophore sensitive to Ca$^{2+}$ Fluo-4 AM (Invitrogen) with a concentration of 5 μM in the presence of 0.02% pluronic acid (F-127, Invitrogen) re-suspended in the standard physiological buffer HBSS (Hank's balanced salt solution) for 40-50 minutes at 37° C. The cover slips were then mounted in an imaging chamber and continuously perfused (1 ml/min) with HBSS (140 mM NaCl, 4 mM KCl, 1 mM MgCl$_2$, 1.8 mM CaCl$_2$, 5 mM D-glucose, 10 mM Hepes (all from Sigma), pH 7.4) at approximately 22° C. The activity of the TRPM8, TRPV1 and TRPA1 channels was evoked by applying short pulses of 10 s of 100 μM menthol, 1 μM capsaicin (CA) or 500 μM mustard oil (MO) using a gravity-activated perfusion system. In every case, a short pulse of high-concentration potassium chloride (40 mM KCl, during 10 s) was applied to ensure the cells responded correctly. The cells that were not sensitive to the application of high potassium concentration were not analysed. The compounds dissolved in the HBSS buffer were applied to the chamber near the cells, keeping the same distance between the cells and the perfusion system under all measurement conditions. The fluorescence measurements were taken using an Axiovert 200 inverted microscope from Zeiss (Oberkochen, Germany) coupled with an ORCA-ER CCD camera (Hamamatsu Photonics, Bridgewater, N.J.) and observed through a 10× magnification air lens. The Fluo-4 AM fluorescent probe was excited at 500 nm using a Lambda-10-2 filter wheel (Sutter Instruments, Novato, Calif.) and the emission fluorescence was filtered with a 535 nm longpass filter. The fluorescence of the individual neurons was monitored as a function of time, delimiting a region of interest in the field that included the cell to be studied and measuring the total fluorescence signal of this region. The images were acquired and processed using the software package of the AquaCosmos computer program (Hamamatsu Photonics). The results obtained have shown that the compound TZM-7 1,2,3-triazole (Compound TZM-7) has a high specificity to activate TRPM8 channels compared with other channels (TRPV1 and TRPA1) (FIG. 1).

Example 29: In Vivo Activity of TRPM8 Agonist Compounds

Figure 2:
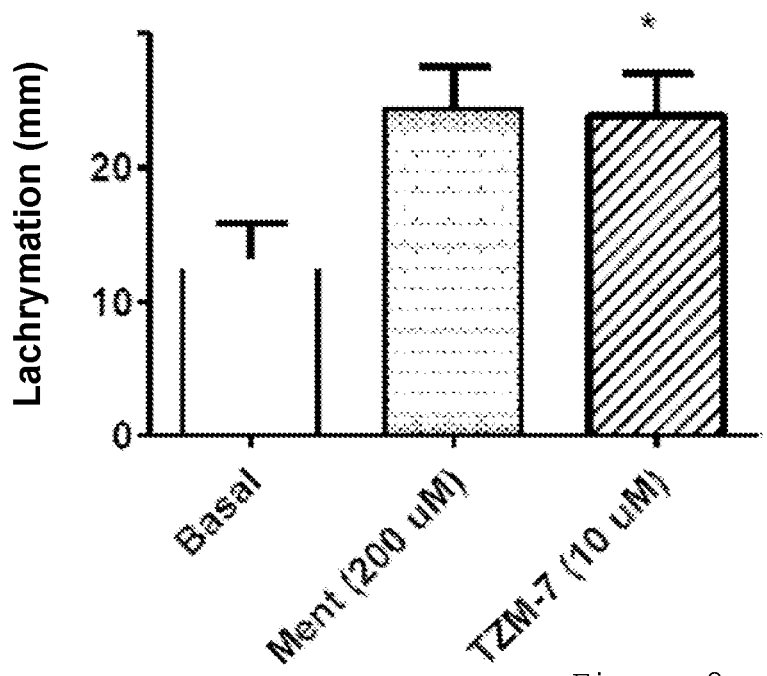
FIG. 2 illustrates tear secretion (mm) in vivo, assessed in an animal model, produced after administration of the compound TZM-7 with a concentration of 10 µM, compared with basal control and menthol with a concentration of 200 µM.

The in vivo activity of the selected TRPM8 activating compounds (TZM-7) has been assessed in an animal model following the protocol described in Acosta M C et al., Invest Ophthalmol Vis Sci 2014 (Corneal sensory nerve activity in an experimental model of UV keratitis. Acosta M et al., Invest Ophthalmol Vis Sci May 1; 55(6):3403-12). Menthol (TRPM8 receptor agonist), instilled ocularly in a guinea pig with a concentration of 200 μM, produces an increase in tear secretion. Tear secretion can be measured using phenol red threads (Zone-Quick, Menicon, Nagoya, Japan) that are applied to the nasal edge of the lower eyelid for 30 seconds (after that time, the distance of the red-dyed thread is measured in mm). Using this technique it has been found that the compound TZM-7 with a concentration of 10 μM significantly increases the rate of lachrymation (p<0.05) and is comparable to the effect of menthol at 200 μM. The results are shown in FIG. 2.

REFERENCES CITED IN THE APPLICATION

Parra A et al, "Tear fluid hyperosmolality increases nerve impulse activity of cold thermoreceptor endings of the cornea", Pain 2014, 155(8), 1481-91.
Carlos Fernandez-Pena et al, "Targeting TRPM8 for Pain Relief", The Open Pain Journal, 2013, 6, (Suppl 1: M15) 154-164).
Nagender P. et al, "Studies on Synthesis of Novel Triazolalkyl Tagged Trifluoromethyl Substituted Pyrimidine Derivatives and their Evaluation for Cytotoxic Activity", Letters in Drug Design & Discovery, 2013, 10,000-000.
Foye's principles of Medicinal Chemistry, Lippicott Williams & Wilkins, Ed. 2008, page 223.
Welschoff N. et al, "Practical Synthesis of Optically Pure Menthylamines Starting from Racemic Neomenthol", Synthesis 2010, 21, 3596-3601.
Utsintong M. et al. "Parallel Synthesis of "Click" Chalcones as Antitubulin Agents", Med. Chem. 2013, 9, 510-516.
Altschul S. F. et al., "Basic Local Alignment Search Tool", J. Mol. Biol. 1990, 215, 403-410.
Bodding et al, "Characterisation of TRPM8 as a pharmacophore receptor", Cell 10 Calcium 2007, 42, 618-628.

The invention claimed is:

1. A compound of formula (I):

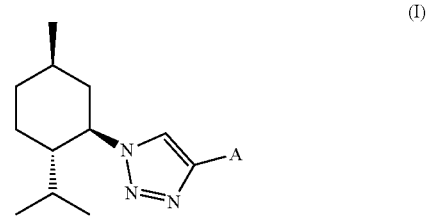

(I)

or a pharmaceutically acceptable salt thereof, or any stereoisomer or mixture of stereoisomers, whether of the compound of formula (I) or of any of the pharmaceutically acceptable salts thereof,
wherein:
A is selected from the group consisting of:
  a) (C$_1$-C$_8$) alkyl optionally substituted by one or more substituents selected between R$^1$ and (C$_6$-C$_{14}$) aryl optionally substituted by one or more substituents R$^2$;
  b) (C$_3$-C$_6$) cycloalkyl optionally substituted by one or more substituents R$^1$;
  c) (C$_5$-C$_{14}$) aryl optionally substituted by one or more substituents R$^3$;
  d) (C$_6$-C$_{14}$) heteroaryl optionally substituted by one or more substituents R$^3$;
  e) C(O)—(C$_6$-C$_{14}$) aryl, wherein the (C$_6$-C$_{14}$) aryl group is optionally substituted by one or more substituents R$^3$;
  f) C(O)—(C$_6$-C$_{14}$) heteroaryl, wherein the (C$_6$-C$_{14}$) heteroaryl group is optionally substituted by one or more substituents R$^3$;
  g) CH(OH)—(C$_6$-C$_{14}$) aryl, wherein the (C$_6$-C$_{14}$) aryl group is optionally substituted by one or more substituents R$^3$; and h) CH(OH)—($C_6$-$C_{14}$) heteroaryl, wherein the ($C_6$-$C_{14}$) heteroaryl group is optionally substituted by one or more substituents $R^3$;

each $R^1$ is selected independently from the group consisting of a halogen atom, —$OR^4$, —CN, —$COOR^4$, —$CONR^4R^5$, —$NR^4R^5$, —$NHCOR^4$, —$NHSO_2R^4$, —S(O)$R^4$, —S(O)$_2R^4$, and —$SO_2NHR^4$;

each $R^2$ is selected independently from the group consisting of a halogen atom, —COOH, —OH, —$NH_2$, —$COOR^6$, —$NO_2$, —$CF_3$, —$OCF_3$, —CN, —$OR^6$, —$CONH_2$, —$CONHR^6$, —$CONR^6R^7$, —$NHR^6$, —$NHCOR^6$, —$NHSO_2R^6$, and —$SO_2NHR^6$;

each $R^3$ is selected independently from the group consisting of a halogen atom, ($C_6$-$C_{14}$) aryl optionally substituted by one or more substituents $R^2$, —$CF_3$, —$COOR^4$, —$CONR^4R^5$, —CN, —$NHR^4$, —$NHCOR^4$, —$NHSO_2R^4$, —$NO_2$, —$OR^4$, —$OCF_3$, and —$SO_2NHR^4$;

$R^4$ and $R^5$ are selected independently from the group consisting of H, ($C_1$-$C_8$) alkyl optionally substituted by one or more substituents $R^8$, ($C_3$-$C_6$) cycloalkyl optionally substituted by one or more substituents $R^8$, ($C_6$-$C_{14}$) aryl optionally substituted by one or more substituents $R^2$, and ($C_6$-$C_{14}$) heteroaryl optionally substituted by one or more substituents $R^2$;

$R^6$ and $R^7$ are selected independently from the group consisting of H, ($C_1$-$C_8$) alkyl optionally substituted by one or more substituents $R^8$ and ($C_3$-$C_6$) cycloalkyl optionally substituted by one or more substituents $R^8$;

each $R^8$ is selected independently from the group consisting of —COOH, —OH, —$NH_2$, $NHR^9$, -halogen, —$COOR^9$, —$NO_2$, —$CF_3$, —$OCF_3$, —CN, —$OR^9$, —$CONH_2$; and $R^9$ is selected from the group consisting of H, ($C_1$-$C_8$) alkyl optionally substituted by one or more halogen atoms and ($C_3$-$C_6$) cycloalkyl optionally substituted by one or more halogen atoms;

with the condition that the compound of formula (I) is different from 4-[[1-[5-methyl-2-(1-methyl-ethyl)cyclohexyl]-1H-1,2,3-triazole-4-yl]methoxy]-6-(trifluoromethyl)-2-pyrimidinamine; and wherein the compound is not 1-((1R,2S,5R)-2-isopropyl-5-methylcyclohexyl)-4-phenyl-1H-1,2,3-triazole or a stereoisomer thereof.

2. The compound according to claim 1, wherein A is selected from the group consisting of:
a) ($C_1$-$C_8$) alkyl optionally substituted by one or more substituents selected between $R^1$ and ($C_6$-$C_{14}$) aryl optionally substituted by one or more substituents $R^2$;
b) ($C_3$-$C_6$) cycloalkyl optionally substituted by one or more substituents $R^1$;
c) ($C_6$-$C_{14}$) aryl optionally substituted by one or more substituents $R^3$;
d) ($C_6$-$C_{14}$) heteroaryl optionally substituted by one or more substituents $R^3$;
e) C(O)—($C_6$-$C_{14}$) aryl, wherein the ($C_6$-$C_{14}$) aryl group is optionally substituted by one or more substituents $R^3$; and
g) CH(OH)—($C_6$-$C_{14}$) aryl, wherein the ($C_6$-$C_{14}$) aryl group is optionally substituted by one or more substituents $R^3$.

3. The compound according to claim 1, wherein A is a) ($C_1$-$C_8$) alkyl optionally substituted by one or more substituents selected from the group consisting of $OR^4$, —CN, —$COOR^4$, and phenyl optionally substituted by one or more substituents $R^2$.

4. The compound according to claim 1, wherein A is b) ($C_3$-$C_6$) cycloalkyl optionally substituted by one or more substituents $R^1$, wherein ($C_3$-$C_6$) cycloalkyl is cyclopropane, cyclobutane or cyclohexane.

5. The compound according to claim 1, wherein A is c) ($C_6$-$C_{14}$) aryl optionally substituted by one or more substituents selected between —$OR^4$ and ($C_6$-$C_{14}$) aryl optionally substituted by one or more substituents $R^2$.

6. The compound according to claim 5, wherein A is c) ($C_6$-$C_{14}$) aryl substituted by one or more substituents —$OR^4$.

7. The compound according to claim 6, wherein ($C_6$-$C_{14}$) aryl is phenyl and $R^4$ is ($C_1$-$C_8$) alkyl.

8. The compound according to claim 1, wherein A is d) unsubstituted ($C_6$-$C_{14}$) heteroaryl.

9. The compound according to claim 1, wherein A is e) C(O)—($C_6$-$C_{14}$) aryl, wherein the ($C_6$-$C_{14}$) aryl group is phenyl and is optionally substituted by one or more substituents selected from the group consisting of a halogen atom, ($C_6$-$C_{14}$) aryl optionally substituted by one or more substituents $R^2$ and —$OR^4$.

10. The compound according to claim 1, wherein A is g) CH(OH)—($C_6$-$C_{14}$) aryl, wherein the ($C_6$-$C_{14}$) aryl group is phenyl and is optionally substituted by one or more substituents —$OR^4$.

11. The compound according to claim 1, selected from the group consisting of:
(1-((1R,2S,5R)-2-isopropyl-5-methylcyclohexyl)-1H-1,2,3-triazole-4-yl)methanol;
1-((1R,2S,5R)-2-isopropyl-5-methylcyclohexyl)-4-(4-phenoxyphenyl)-1H-1,2,3-triazole;
1-((1R,2S,5R)-2-isopropyl-5-methylcyclohexyl)-4-(4-methoxyphenyl)-1H-1,2,3-triazole;
4-([1,1'-biphenyl]-4-yl)-1-((1R,2S,5R)-2-isopropyl-5-methylcyclohexyl)-1H-1,2,3-triazole;
1-(1-((1R,2S,5R)-2-isopropyl-5-methylcyclohexyl)-1H-1,2,3-triazole-4-yl)cyclohexan-1-ol;
4-(3,5-dimethoxyphenyl)-1-((1R,2S,5R)-2-isopropyl-5-methylcyclohexyl)-1H-1,2,3-triazole;
1-((1R,2S,5R)-2-isopropyl-5-methylcyclohexyl)-4-(naphthalene-1-yl)-1H-1,2,3-triazole;
2-(1-((1R,2S,5R)-2-isopropyl-5-methylcyclohexyl)-1H-1,2,3-triazole-4-yl)pyridine;
1-((1R,2S,5R)-2-isopropyl-5-methylcyclohexyl)-4-phenethyl-1H-1,2,3-triazole;
(3,4-dimethoxyphenyl)(1-((1R,2S,5R)-2-isopropyl-5-methylcyclohexyl)-1H-1,2,3-triazole-4-yl)methanone;
(3-fluorophenyl)(1-((1R,2S,5R)-2-isopropyl-5-methylcyclohexyl)-1H-1,2,3-triazole-4-yl)methanone;
(1-((1R,2S,5R)-2-isopropyl-5-methylcyclohexyl)-1H-1,2,3-triazole-4-yl)(4-phenoxyphenyl)methanone;
(2,4-dimethoxyphenyl)(1-((1R,2S,5R)-2-isopropyl-5-methylcyclohexyl)-1H-1,2,3-triazole-4-yl)methanone;
(1-((1R,2S,5R)-2-isopropyl-5-methylcyclohexyl)-1H-1,2,3-triazole-4-yl)(2-methoxyphenyl)methanone;
(3,5-dimethoxyphenyl)(1-((1R,2S,5R)-2-isopropyl-5-methylcyclohexyl)-1H-1,2,3-triazole-4-yl)methanone;
[1,1'-biphenyl]-4-yl(1-((1R,2S,5R)-2-isopropyl-5-methylcyclohexyl)-1H-1,2,3-triazole-4-yl)methanone;
(1-((1R,2S,5R)-2-isopropyl-5-methylcyclohexyl)-1H-1,2,3-triazole-4-yl)(4-methoxyphenyl)methanone;
1-((1R,2S,5R)-2-isopropyl-5-methylcyclohexyl)-1H-1,2,3-triazole-4-yl)(3-methoxyphenyl)methanone;
(4-chlorophenyl)(1-((1R,2S,5R)-2-isopropyl-5-methylcyclohexyl)-1H-1,2,3-triazole-4-yl)methanone;
9-(1-((1R,2S,5R)-2-isopropyl-5-methylcyclohexyl)-1H-1,2,3-triazole-4-yl)-nonanoic acid;

5-(1-((1R,2S,5R)-2-isopropyl-5-methylcyclohexyl)-1H-1,2,3-triazole-4-yl)pentanenitrile;
3-[1-((1R,2S,5R)-2-isopropyl-5-methylcyclohexyl)-1H-1,2,3-triazole-4-yl]phenol;
1-((1R,2S,5R)-2-isopropyl-5-methylcyclohexyl)-4-(3-methoxyphenyl)-1H-1,2,3-triazole;
1-((1R,2S,5R)-2-isopropyl-5-methylcyclohexyl)-4-(methoxymethyl)-1H-1,2,3-triazole; and
(3,4-dimethoxyphenyl)(1-((1R,2S,5R)-2-isopropyl-5-methylcyclohexyl)-1H-1,2,3-triazole-4-yl)methanol.

12. The compound of claim 1, wherein A is:
a) $(C_1-C_8)$ alkyl optionally substituted by one or more substituents selected between $R^1$ and $(C_6-C_{14})$ aryl optionally substituted by one or more substituents $R^2$;
b) $(C_3-C_6)$ cycloalkyl optionally substituted by one or more substituents $R^1$;
c) $(C_6-C_{14})$ aryl substituted by one or more substituents $R^3$;
d) $(C_6-C_{14})$ heteroaryl optionally substituted by one or more substituents $R^3$;
e) $C(O)$—$(C_6-C_{14})$ aryl, wherein the $(C_6-C_{14})$ aryl group is optionally substituted by one or more substituents $R^3$;
f) $C(O)$—$(C_6-C_{14})$ heteroaryl, wherein the $(C_6-C_{14})$ heteroaryl group is optionally substituted by one or more substituents $R^3$;
g) $CH(OH)$—$(C_6-C_{14})$ aryl, wherein the $(C_6-C_{14})$ aryl group is optionally substituted by one or more substituents $R^3$; or
h) $CH(OH)$—$(C_6-C_{14})$ heteroaryl, wherein the $(C_6-C_{14})$ heteroaryl group is optionally substituted by one or more substituents $R^3$.

13. The compound of claim 1, wherein A is c) $(C_6-C_{14})$ aryl substituted by one or more substituents $R^3$.

14. The compound of claim 1, wherein $R^4$ is independently selected from the group consisting of H, $(C_1-C_8)$ alkyl optionally substituted by one or more substituents $R^8$, $(C_3-C_6)$ cycloalkyl optionally substituted by one or more substituents $R^8$, $C_{14}$ aryl optionally substituted by one or more substituents $R^2$, and $(C_6-C_{14})$ heteroaryl optionally substituted by one or more substituents $R^2$.

15. The compound of claim 1, wherein each $R^1$ is selected independently from the group consisting of a halogen atom, —CN, —COOR$^4$, —CONR$^4$R$^5$, —NR$^4$R$^5$, —NHCOR$^4$, —NHSO$_2$R$^4$, —S(O)R$^4$, —S(O)$_2$R$^4$, and —SO$_2$NHR$^4$.

16. The compound of claim 1, wherein $R^4$ is selected independently from the group consisting of H, $(C_1-C_8)$ alkyl optionally substituted by one or more substituents $R^8$, $(C_3-C_6)$ cycloalkyl optionally substituted by one or more substituents $R^8$, $(C_6-C_{14})$ aryl substituted by one or more substituents $R^2$, and $(C_6-C_{14})$ heteroaryl optionally substituted by one or more substituents $R^2$; and
each $R^2$ is selected independently from the group consisting of —COOH, —OH, —NH$_2$, —COOR$^6$, —NO$_2$, —CF$_3$, —OCF$_3$, —CN, —OR$^6$, —CONH$_2$, —CONHR$^6$, —CONR$^6$R$^7$, —NHR$^6$, —NHCOR$^6$, —NHSO$_2$R$^6$, and —SO$_2$NHR$^6$.

17. The compound of claim 1, wherein A is selected from the group consisting of:
a) $(C_1-C_8)$ alkyl optionally substituted by one or more substituents selected between $R^1$ and $(C_6-C_{14})$ aryl optionally substituted by one or more substituents $R^2$;
b) $(C_3-C_6)$ cycloalkyl optionally substituted by one or more substituents $R^1$;
c) $(C_6-C_{14})$ aryl substituted by one or more $R^3$, or $C_{14}$ aryl;
d) $(C_6-C_{14})$ heteroaryl optionally substituted by one or more substituents $R^3$;
e) $C(O)$—$(C_6-C_{14})$ aryl, wherein the $(C_6-C_{14})$ aryl group is optionally substituted by one or more substituents $R^3$;
f) $C(O)$—$(C_6-C_{14})$ heteroaryl, wherein the $(C_6-C_{14})$ heteroaryl group is optionally substituted by one or more substituents $R^3$;
g) $CH(OH)$—$(C_6-C_{14})$ aryl, wherein the $(C_6-C_{14})$ aryl group is optionally substituted by one or more substituents $R^3$; and
h) $CH(OH)$—$(C_6-C_{14})$ heteroaryl, wherein the $(C_6-C_{14})$ heteroaryl group is optionally substituted by one or more substituents $R^3$.

18. The compound of claim 14, wherein A is selected from the group consisting of:
a) $(C_1-C_8)$ alkyl optionally substituted by one or more substituents selected between $R^1$ and $(C_6-C_{14})$ aryl optionally substituted by one or more substituents $R^2$;
b) $(C_3-C_6)$ cycloalkyl optionally substituted by one or more substituents $R^1$;
c) $(C_6-C_{14})$ aryl substituted by one or more substituents $R^3$, or $C_{14}$ aryl;
d) $(C_6-C_{14})$ heteroaryl optionally substituted by one or more substituents $R^3$;
e) $C(O)$—$(C_6-C_{14})$ aryl, wherein the $(C_6-C_{14})$ aryl group is optionally substituted by one or more substituents $R^3$;
f) $C(O)$—$(C_6-C_{14})$ heteroaryl, wherein the $(C_6-C_{14})$ heteroaryl group is optionally substituted by one or more substituents $R^3$;
g) $CH(OH)$—$(C_6-C_{14})$ aryl, wherein the $(C_6-C_{14})$ aryl group is optionally substituted by one or more substituents $R^3$; and
h) $CH(OH)$—$(C_6-C_{14})$ heteroaryl, wherein the $(C_6-C_{14})$ heteroaryl group is optionally substituted by one or more substituents $R^3$.

19. The compound of claim 15, wherein A is selected from the group consisting of:
a) $(C_1-C_8)$ alkyl optionally substituted by one or more substituents selected between $R^1$ and $(C_6-C_{14})$ aryl optionally substituted by one or more substituents $R^2$;
b) $(C_3-C_6)$ cycloalkyl optionally substituted by one or more substituents $R^1$;
c) $(C_6-C_{14})$ aryl substituted by one or more substituents $R^3$, or $C_{14}$ aryl;
d) $(C_6-C_{14})$ heteroaryl optionally substituted by one or more substituents $R^3$;
e) $C(O)$—$(C_6-C_{14})$ aryl, wherein the $(C_6-C_{14})$ aryl group is optionally substituted by one or more substituents $R^3$;
f) $C(O)$—$(C_6-C_{14})$ heteroaryl, wherein the $(C_6-C_{14})$ heteroaryl group is optionally substituted by one or more substituents $R^3$;
g) $CH(OH)$—$(C_6-C_{14})$ aryl, wherein the $(C_6-C_{14})$ aryl group is optionally substituted by one or more substituents $R^3$; and
h) $CH(OH)$—$(C_6-C_{14})$ heteroaryl, wherein the $(C_6-C_{14})$ heteroaryl group is optionally substituted by one or more substituents $R^3$.

20. The compound of claim 16, wherein A is selected from the group consisting of:
a) $(C_1-C_8)$ alkyl optionally substituted by one or more substituents selected between $R^1$ and $(C_6-C_{14})$ aryl optionally substituted by one or more substituents $R^2$;
b) $(C_3-C_6)$ cycloalkyl optionally substituted by one or more substituents $R^1$;

c) $(C_6-C_{14})$ aryl substituted by one or more substituents $R^3$, or $C_{14}$ aryl;
d) $(C_6-C_{14})$ heteroaryl optionally substituted by one or more substituents $R^3$;
e) $C(O)-(C_6-C_{14})$ aryl, wherein the $(C_6-C_{14})$ aryl group is optionally substituted by one or more substituents $R^3$;
f) $C(O)-(C_6-C_{14})$ heteroaryl, wherein the $(C_6-C_{14})$ heteroaryl group is optionally substituted by one or more substituents $R^3$;
g) $CH(OH)-(C_6-C_{14})$ aryl, wherein the $(C_6-C_{14})$ aryl group is optionally substituted by one or more substituents $R^3$; and
h) $CH(OH)-(C_6-C_{14})$ heteroaryl, wherein the $(C_6-C_{14})$ heteroaryl group is optionally substituted by one or more substituents $R^3$.

\* \* \* \* \*